US007309783B2

(12) United States Patent
Hansen et al.

(10) Patent No.: US 7,309,783 B2
(45) Date of Patent: Dec. 18, 2007

(54) MAMMALIAN EARLY DEVELOPMENTAL REGULATOR GENE

(75) Inventors: Marc F. Hansen, New Hartford, CT (US); Amit Deshpande, Farmington, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 10/142,275

(22) Filed: May 9, 2002

(65) Prior Publication Data

US 2006/0116338 A1    Jun. 1, 2006

Related U.S. Application Data

(60) Provisional application No. 60/289,767, filed on May 9, 2001.

(51) Int. Cl.
C12N 15/11 (2006.01)
C12N 15/00 (2006.01)
C12N 5/00 (2006.01)

(52) U.S. Cl. .................. 536/23.1; 435/320.1; 435/325

(58) Field of Classification Search ..................... None
See application file for complete search history.

(56) References Cited

U.S. PATENT DOCUMENTS

| | | |
|---|---|---|
| 4,714,681 A | 12/1987 | Reading |
| 4,853,230 A | 8/1989 | Lovgren et al. |
| 4,946,778 A | 8/1990 | Ladner et al. |
| 5,093,246 A | 3/1992 | Cech et al. |
| 5,223,409 A | 6/1993 | Ladner et al. |
| 5,270,163 A | 12/1993 | Gold et al. |
| 5,270,170 A | 12/1993 | Schatz et al. |
| 5,283,173 A | 2/1994 | Fields et al. |
| 5,422,120 A | 6/1995 | Kim |
| 5,633,135 A | 5/1997 | Croce et al. |
| 5,633,136 A | 5/1997 | Croce et al. |
| 5,641,670 A | 6/1997 | Treco et al. |
| 5,698,686 A | 12/1997 | Gottschling et al. |
| 5,714,353 A | 2/1998 | Pathak et al. |
| 5,741,486 A | 4/1998 | Pathak et al. |
| 5,914,266 A | 6/1999 | Randazzo |
| 5,916,752 A | 6/1999 | Gottschling et al. |
| 5,935,811 A | 8/1999 | Anderson et al. |
| 5,948,640 A | 9/1999 | Randazzo |
| 5,955,594 A | 9/1999 | Mishra |
| 6,004,528 A | 12/1999 | Bergstein |
| 6,040,140 A | 3/2000 | Croce et al. |
| 6,060,588 A | 5/2000 | Li et al. |
| 6,083,742 A | 7/2000 | Randazzo |
| 6,096,534 A | 8/2000 | Barsov et al. |
| 6,103,886 A | 8/2000 | Lahn et al. |
| 6,140,111 A | 10/2000 | Riviere et al. |
| 6,140,483 A | 10/2000 | Randazzo |
| 6,166,191 A | 12/2000 | Randazzo |
| 6,190,907 B1 | 2/2001 | Kim et al. |
| 6,194,557 B1 | 2/2001 | Li et al. |

FOREIGN PATENT DOCUMENTS

| | | |
|---|---|---|
| EP | 0 524 968 B1 | 3/1991 |
| WO | WO 92/06204 | 4/1992 |

OTHER PUBLICATIONS

Stephen M. Edgington. "Is biopharmaceutical discovery entering a new evolutionary stage?" Bio/Technology. vol. 11. pp. 285-289. Mar. 1993.
Hansen, et al. "Osteosarcoma and retinoblastoma: A shared chromosomal mechanism revealing recessive predisposition". Proc. Natl. Acad. Sci. USA. vol. 82. pp. 6216-6220. Sep. 1985.
Keppler-Noreull, et al. "Chromosome 18q Paracentric Inversion in a Family with Mental Retardation and Hearing Loss". American Journal of Medical Genetics. vol. 76. pp. 372-378. (1998).
T. Ikeuchi. "Inhibitory effect of ethidium bromide on mitotic chromosome condensation and its application to high-resolution chromosome banding". Cytogenet. Cell Genet. vol. 38, pp. 56-61 (1984).
Findeis, et al. "Targeted delivery of DNA for gene therapy via receptors". Trends in Biotechnology. vol. 11. pp. 202-205 (1993).
Orlandi, et al. "Cloning immunoglobulin variable domains for expression by the polymerase chain reaction". Proc. Natl. Acad. Sci. USA. vol. 86. pp. 3833-3837. May 1989.
Skerra, et al. "Assembly of a Functional Immunoglobulin Fv Fragment in *Escherichia coli*".Science. vol. 240. pp. 1038-1041 (1998).
Better, et al. "*Escherichia coli* Secretion of an Active Chimeric Antibody Fragment". Science vol. 240. pp. 1041-1043. (1988).
Sorge, et al.. "Amphotropic Retrovirus Vector System for Human Cell Gene Transfer". Molecular and Cellular Biology. pp. vol. 4. No. 9. pp. 1730-1737. Sep. 1984.
Fred D. Ledley. "Pharmaceutical Approach to Somatic Gene Therapy". Pharmaceutical Research. vol. 13. No. 11. pp. 1595-1614. 1996.
Wu, et al., "Receptor-mediated Gene Delivery and Expression in Vivo" The Journal of Biological Chemistry. vol. 263, No. 29, Issue of Oct. 15, 1988. pp. 14621-14624.
Wu, et al., "Receptor-mediated Gene Delivery in Vivo" The Journal of Biological Chemistry. vol. 266, No. 22 Issue of Aug. 5, 1991. pp. 14338-14342.
Wu, et al., "Incorporation of Adenovirus into a Ligand-based DNA Carrier System Results in Retention of Original Receptor Specificity and Enhances Targeted Gene Expression" The Journal of Biological Chemistry. vol. 269, No. 15, Issue of Apr. 15, 1994. pp. 11542-11546.
DeWitt, et al. ""Diversomers": An approach to nonpeptide,nonoligomeric chemical diversity" Proc. Natl. Acad. Sci. USA. vol. 90, pp. 6909-6913, Aug. 1993.

(Continued)

Primary Examiner—Peter Paras, Jr.
Assistant Examiner—Marcia S. Noble
(74) Attorney, Agent, or Firm—Cantor Colburn LLP

(57) ABSTRACT

This disclosure encompasses the edr3 polynucleotide, polypeptides encoded by the edr3 gene and fragments thereof. This disclosure also encompasses homologues of the edr3 gene from mammals, in particular from humans. In addition, this disclosure encompasses the use of edr3 polynucleotides, edr3 proteins and polypeptides, and antibodies to the edr3 protein capable of increasing or decreasing edr3 activity or expression.

6 Claims, 10 Drawing Sheets

OTHER PUBLICATIONS

Zenke, et al. "Receptor-mediated endocytosis of transferrin-polycation conjugates: An efficient way to introduce DNA into hematopoietic cells". Proc. Natl. Acad. Sci. USA vol. 87, pp. 3655-3659, May 1990.

Cunningham, et al. "High-Resolution Epitope Mapping of hGH-Receptor Interactions by Alanine-Scanning Mutagenesis". Science 244. pp. 1081-85. 1989.

Reidhaar-Olson, et al., "Combinatorial Cassette Mutagenesis as a Probe of the Informational Content of Protein Sequences" Science 241. pp. 53-57. 1988.

Szybalska and Szybalski "Genetics of Human Cell Lines, IV. DNA-Mediated Heritable Transformation of a Biochemical Trait" Proc. Nat. Acad. Sci., USA. vol. 48. pp. 2026-2034. 1962.

Maitland, et al. "Biochemical Transformation of Mouse Cells by Fragments of Herpes Simplex Virus DNA" Cell, vol. 11, pp. 233-241. May 1977.

van der Putten, et al. "Efficient insertion of genes into the mouse germ line via retroviral vectors". Proc. Natl. Acad. Sci.USA vol. 82. pp. 6148-6152. Sep. 1985.

De Vos, et al . "Human Growth Hormone and Extracellular Domain of Its Receptor: Crystal Structure of the Complex". Science, vol. 255. pp. 306-312. 1992.

Tsai, et al. "In Vitro Selection of RNA Epitopes Using Autoimmune Patient Serum" The Journal of Immunology. vol. 150. No. 3. pp. 1137-1145. Feb. 1, 1993.

Cull, et al. "Screening for receptor ligands using large libraries of peptides linked to the C terminus of the lac repressor". Proc. Natl. Acad. Sci. USA vol. 89, pp. 1865-1869. Mar. 1992.

Cho, et al. "An Unnatural Biopolymer" Science. vol. 261. pp. 1303-1307. Sep. 3, 1993.

Simon, et al. "Peptoids: A modular approach to drug discovery". Proc. Natl. Acad. Sci. USA vol. 89. pp. 9367-9371. Oct. 1992.

Fodor, et al., "Multiplexed biochemical assay with biological chips". Nature. vol. 364. pp. 555-556. Aug. 5, 1993.

Lam, et al. "A new type of synthetic peptide library for identifying ligand-binding activity". Nature. vol. 354. pp. 82-84. Nov. 7, 1991.

Gallop, et al. "Applications of Combinatorial Technologies to Drug Discover. 1. Background and Peptide Combinatorial Libraries." Journal of Medical Chemistry. vol. 37. No. 9. pp. 1233-1251. Apr. 29, 1994.

Scott, et al. "Searching for Peptide Ligands with an Epitope Library". Science. vol. 249. pp. 386-390. Jul. 27, 1990.

Felici, et al. "Selection of Antibody Ligands from a Large Library of Oligopeptides Expressed on a Multivalent Exposition Vector". J. Mol. Biol. vol. 222. pp. 301-310. 1991.

Carell, et al., "A Solution-Phase Screening Procedure for the Isolation of Active Compounds from a Library of Molecules". Angew. Chem. Int. Ed. Engl. vol. 33 No. 20. pp. 2061-2064. 1994.

Carell, et al. "A Novel Procedure for the Synthesis of Libraries Containing Small Organic Molecules". Angew. Chem. Int. Ed. Engl. vol. 33. No. 20. pp. 2059-2061. 1994.

Tsai, et al. "In vitro selection of an RNA epitope immunologically cross-reactive with a peptide". Proc. Natl. Acad. Sci.USA. vol. 89. pp. 8864-8868. Oct. 1992.

Lowy, et al. "Isolation of Transforming DNA: Cloning the Hamster aprt Gene". Cell. vol. 22, pp. 817-823. Dec. 1980.

Wlodaver, et al. "Crystal structure of human recombinant interleukin-4 at 2.25 A resolution" FEBS letters. vol. 309. No. 1. pp. 59-64. Aug. 1992.

Bowie, et al. "Identifying determinants of folding and activity for a protein of unknown structure". Proc. Natl. Acad. Sci. USA. vol. 86. pp. 2152-2156. Apr. 1989.

Bass, et al. "A systematic mutational analysis of hormone-binding determinants in the human growth hormone receptor". Proc. Natl. Acad. Sci. USA. vol. 88. pp. 4498-4502. May 1991.

Lowman, et al. "Selecting High-Affinity Binding Proteins by Monovalent Phage Display". Biochemistry. vol. 30. pp. 10832-10838. 1991.

Smith, et al. "Human Interleukin 4., The Solution Structure of a Four-helix Bundle Protein", Human Interleukin 4. J. Mol. Biol. vol. 224. pp. 899-904. 1992.

Logan, et al. "Adenovirus tripartite leader sequence enhances translation of mRNAs late after infection". Proc. Natl. Acad. Sci. USA. vol. 81. pp. 3655-3659. Jun. 1984.

Kohl, et al. "Selective Inhibition of ras-Dependent Transformation by a Farnesyltrase Inhibitor". Science. vol. 260. pp. 1934-1937. Jun. 1993.

Lam, et al. "Rational Design of Potent, Bioavailable, Nonpeptide Cyclic Ureas as HIV Protease Inhibitors". Science. vol. 263. pp. 380-383. Jan. 1994.

Fire, et al. "Potent and specific genetic interference by double-stranded RNA in Caenorhabditis elegans". Nature. vol. 391. pp. 806-811. Feb. 1998.

Barbas, et al. "Combinatorial Immunoglobulin Libraries on the Surface of Phage (Phabs): Rapid Selection of Antigen-Specific Fabs". METHODS: A Companion to Methods in Enzymology. vol. 2. No. 2 pp. 119-124. Apr. 1991.

Ner, et al. "A Simple and Efficient Procedure for Generating Random Point Mutations and for Codon Replacements Using Mixed Oligodeoxnucleotides". DNA. vol. 7. No. 2. pp. 127-134. 1988.

Derbyshire, et al. "A simple and efficient procedure for saturation mutagenesis using mixed oligodeoxynucleotides" Gene. vol. 46. pp. 145-152. 1986.

Jones, et al. "Replacing the complementarity-determining regions in a human antibody with those from a mouse". Nature. vol. 321. pp. 522-525. May 1986.

Karjalainen, et al. "An unusual type of V-J joining diversifies the primary repertoire of mouse 1 light chains". Nature. vol. 314. pp. 544-546. Apr. 1985.

Zuckermann, et al. Discovery of Nanomolar Ligands for 7-Transmembrane G-Protein-Coupled Receptors from a Diverse N-(Substituted) glycine Peptoid Library. J. Med. Chem. vol. 37. pp. 2678-2685. 1994.

Cwirla, et al. "Peptides on phage: A vast library of peptides for identifying ligands". Proc. Natl. Acad. Sci. USA. vol. 87. pp. 6378-6382. Aug. 1990.

Erb, et al. "Recursive deconvolution of combinatorial chemical libraries". Proc. Natl. Acad. Sci. USA vol. 91. pp. 11422-11426. Nov. 1994.

Singer, et al. "Optimal Humanization of 1B4, an Anit-CD18 Murine Monoclonal Antibody, Is Achieved by Correct Choice of Human V-Region Framework Sequences". The Journal of Immunology. vol. 150. pp. 2844-2857. Apr. 1, 1993.

John Wiley & Sons. Current Protocols in Immunology.Sections 2.4.1 to 2.4.7 Mar. 19, 1993.

Edgington. Shape Space. Is biopharmaceutical discovery entering a new eveolutionary stage?. Bio/Technology vol. 11. pp. 285-289. Mar. 1993.

Bitter, et al. "Expression and Secretion vectors for Yeast". Methods in Enzymology. vol. 153. No. 33. pp. 516-545. 1987.

Houghten, et al.; "The Use of Synthetic Peptide Combinatorial Libraries for the Identification of Bioactive Peptides"; BioTechniques; 13; pp. 412-420; 1992.

EP0827545 English Abstract Publication date Aug. 1, 2000.

WO 91/16116 English Abstract Publication date Oct. 31, 1991.

EP0225189 English Abstract Publication Date Mar. 20, 1990.

EP0524968 English Abstract Publication Date Oct. 3, 1991.

WO 95/13796 English Abstract Publication Date May 26, 1995.

Accession No. AF380154, Publication date Jun. 2, 2002.

Accession No. AA808201, Entry date Feb. 12, 1998.

Accession No. AA810014, Entry date Mar. 17, 1998.

AU9230801 English Abstract Publication Date Apr. 15, 2002.

FIG. 3A

```
DR3   MDTEPNPGTSSVSTT TSSTTTTTTTTSSSR MQQPQISVYSGSDRH AVQVFQQALHRPPSS AAQYLQQMYAAQQQH
Edr3  MDSEPSSGTS-VSTT ASTTTTTTTTSSSR  MQQPQISVYSGSDRH AVQVIQQALHRPPSS AAQYLQQMYAAQQQH
DR2   --------------- --------------- --------------- --------------- ---------------
DR1   METE------SEQN  SNSTNGSSSSGGSSR PQIAQMSLYERQAVQ ALQALQRQPNAAQYF HQFMLQQQLSNAQLH   88
      --LMLHTAALQQQHL SSSQLQSLAAVQASL SSGRPSTSPTGSVTQ QSSMSQASSSTSGSI TQQTMLLGSTSPTLT   87
      --LMLHTAALQQQHL SSSQLQSLAAVQASL SSGRPSTSPTGSVTQ LMNRSQTSSSTSGSI TQQTMLLGSTSPTLT    0
      --------------- --------------- --------------- --------------- ---------------   83

DR3   SLAAVQQATIAASRQ ASSPNTSTTQQQTTT TQASINLATTSAAQL ISRSQSVSSPSATTL TQSVLLGNTTSPPLN
Edr3  ASQAQMYLRAQ---- --------------- MLIFTPATTVAAVQS DIPVVSSS--SSSSC QSAATQVNLTLRSQ
DR2   ASQAQMYLRAQ---- --------------- MLIFTPATTVAAVQS DIPVVSSS--PSPSC QSAAAQVNLTLRSQ
DR1   QSQAQMYLRPQLGNL LQVNRTPGSNVPLAS QLILMPNGAVAAVQQ EVPSAQSPGVHADAD QVQNLAVRNQQASAQ  247
      KLGVLSSSQNGPPKS TSQTQSLTICHNKTT VTSSKISQRDPSPES NKKGESPSLESRSTA VTRTSSIHQLIAPAS  246
      KLGVLSSSQNGPPKS AGQTQSLTICHNKTT VTSSKISQRDPSPES -KKGGSPGLESRSTA VTRTSSIHQLIAPAS    0

DR3   GPQMQGSTQKAIPPG ASPVSSLSQASSQAL AVAQASSGATNQSLN LSQAGGGSGNSIPGS MGPGGGQAHGGLGQ   263
      YSPIQPHSLIKHQQI PLHSPPSKVSHHQLI LQQQQQQIQPITLQN STQDPPPSQHCIPLQ NHGLPPAPSNAQSQH
      YSPIQPHSLIKHQQI PLHSPPPKVSHHQLL LQQQQQQIQPITLQS PSQDPPPSQHCIPLP NHGLSPAPSNAQPQH
DR2   --------------- --------------- ---MCLRG        GCSPRAPAAAPQPRP PPALPPRPR------
DR1   LPSSGMGGGSCPRKG TGVVQPLPAAQTVTV SQGSQTEAESAAAKK AEADGSGQQNVGMNL TRTATPAPSQTLISS

DR3   CSPIQSHPSPLTVSP NQSQSAQQSVVVSPP PPHSPSQSPTIIIHP QALIQPHPLVSSALQ PGPNLQQSTANQVQA  427
dr3   CSPVQSHPPPLTVSP NQAQSAQQSVVVSPP PPHSPSQSPTIIIHP QALIQPHPLVSSALQ TGPNLQQAAADQVQS  425
DR2   --------------- --------------- --------------- --------------- ---------------   29
DR1   ATYTQIQPHSLIQQQ QQIHLQQKQVVIQQQ IAIHQQQFQHR--Q  SQLLHTATHLQLAQQ QQQQQQQQQQQQPQ   441
      TAQLNLPSHLPLPAS PVVHIGPVQQSALVS PGQQIVSPS-HQQY- SSLQSSPIPIASPPQ MSTSPPAQI------
      TAQLNLPSHLPLPAS PVVHIGPVQQSALVS PGQMIVSPTSHQQY- SALQSSPIPIATPPQ MSASPPAQL------
      ---APVPAS       ---R            PGRPLLTPA-----  -------R------- ---------------

DR1   ATTLTAPQPPQVPPT QQVPPSQSQQQAQTL VVQPMLQSSPLSLPP DAAPKPPIPIQSKPP VAPIKPPQLGAAKMS  503
DR3   ------PPLPLQSMQ SLQVQPEILSQGQVL VQNALVSEEELPAAE ALVQLPFQTLPPPQT VAVNLQVQPPAPVDP  502
dr3   ------PPLPLQSMQ SLQVQPEILSQGQVL VQNALVSEEELPAAE ALVQLPFQTLPPPQT VAVNLQVQPPAPVDP
DR2   --------------- --------------- --------------- -----P--------- ---------------   46
DR1   AAQQPPPHIPVQVVG TRQPGTAQAQAIGLA QLAAAVPTSRGMPGT VQSGQALKASSPPSS QAPGALQECPPTLAP  531
```

FIG. 3B

```
DR3   PVVYQVEDVCEEEMP  EESDECVRMDRTPPP  PTLSPAAITVGRGED  LTSEHPLLEQVELPA  VASV-----------
dr3   PVVYQVEDVCEEEMP  EESDECARMDRTPPP  PTLSPAAVTVGRGED  LTSEHPLLEQVELPA  VASV-----------
DR2   ---------------  -----CGRMRRGSPG  PRLGGSRGERRRPAG  RDPARVGPGQGLRRP  ARPG-----------
DR1   GMTLAPVQGTAHVVK  GGATTSTPVVAQVPA  AFYMQSVHLPGKPQT  LAVKRKADSEEERDD  VSTLGSMLPAKASPV   660
                                                                                          659
      ---------------  --SAS VIKSPSDPSHVSVPP  PPLLLPAATTRSNST  SMHSSIPSI ENKPPQ  AIVKPQILTHVIEGF   124
      ---------------  --SAS VIKSPSDPTHASAPA  PPLLIPAASTRSSST  SLASSTPSL ENKPPQ  AIVKPQILTHVIEGF   711
      ---------------  ---PAA WTETGQIVHALTDL  SIPGMTSGNGNSASS  IAGTAPQNG ENKPPQ  AIVKPQILTHVIEGF
      AESPKVMDEKSSLGE  KAESVANVNANTPSS  ELVALTPAPSVPPPT  LAMVSRQMQ DSKPPQ  AIVKPQILTHVIEGF

DR3   VIQEG LEPFPVSRSS  LLIEQPVKKRPLLDN  QVINSVCVQPELQNN  TKHADNSSDTEMEDM  IAEETLEEMDSE LLK    834
dr3   VIQEG LEPFPVSRSS  LLIEQPVKKRPLLDN  QVVNSVCVQPELQNN  TKHADNSSDTEIEDM  MAEETLEEMDSE LLK    833
DR2   VIQEG AD-VSRWDAR  LLVGNLKKKY----A  QG------FLPEKLPQ QDHT-TTTDSEMEEP  YLQESKEEGAPL KLK    285
DR1   VIQEG AEPFPGGCSQ  LLKESEKPLQTG---  -------LPTGLTE  NQSG------GPFGV DSPSAELDKKAN LLK    874

CEFCGKMGYANEFLR  SKRFCTMSCAKRYNV  SCSKKFAL SRWNRKP DNQS--LGHRGRRPS GPDG---AAREHIL
      CEFCGKMGYPNEFLR  SKRFCTMSCAKRYNV  SCSKKFAL SRWNRKP DNQS--LGHRGRRPS GPEG---AAREHIL
      CELCGRVDFAYKFKR  SKRFCSMACAKRYNV  GCTKRVGI FHSDRSK LQKAGAATHNRRRPA KP------VCHHL
      CEYCGKYAYPEQERG  SKRFCSMTCAKRYNV  SCSHQFRL KRKKMKE FQEANYARVRRRGPR RSSSDIARAKIQGKC

RQLPITYPSAEEDLA  SHEDSVPSAMTTRLR  RQSERERERELRDVR  IRKMPENSDLLPVAQ  TEPSI-----------
      RQLPITYPSAEEDVA  SHEDPVPSAMTTRLR  RQSERERERELRDVR  IRKMPENSDLLPVAQ  TEPSI-----------    963
      PRIPRSSQQALCPFR  LLLLCVTHSQEDSSR  CSDNSSYEEPLSPIS  ASSSTSAGDKASGTW  SSPTCICGTWWAWDT     433
      HRGQEDSSRGSDNSS  YDEALSPTSPGPLSV  RAGHGERDLGNPNTA  PPTPELHGINPVFLS  SNPSR-----------    1004

---------------  ---WTVDDVW AFIHSLPGCQDIADE FRAQEIDGQALLLIK EDHLMSAMNIKLGPA LKICARINSLKES
      ---------------  ---WTVDDVW AFIHSLPGCQDVADE FRAQEIDGQALLLIK EDHLMSAMNMKLGPA LKICARINSLKDS
      ---------------  ---VNVEDVY EFIRSLPGCQEIAEE FRAQEIDGQALLLLK EDHLMSVMNIKLGPA LKIYARISMLKDS
      ---------------  ---WSVEEVY EFIASLQGCQEIAEE FRSQEIDGQAFLLLK EEHLMSAMNIKLGPA LKICAKINVLKET
```

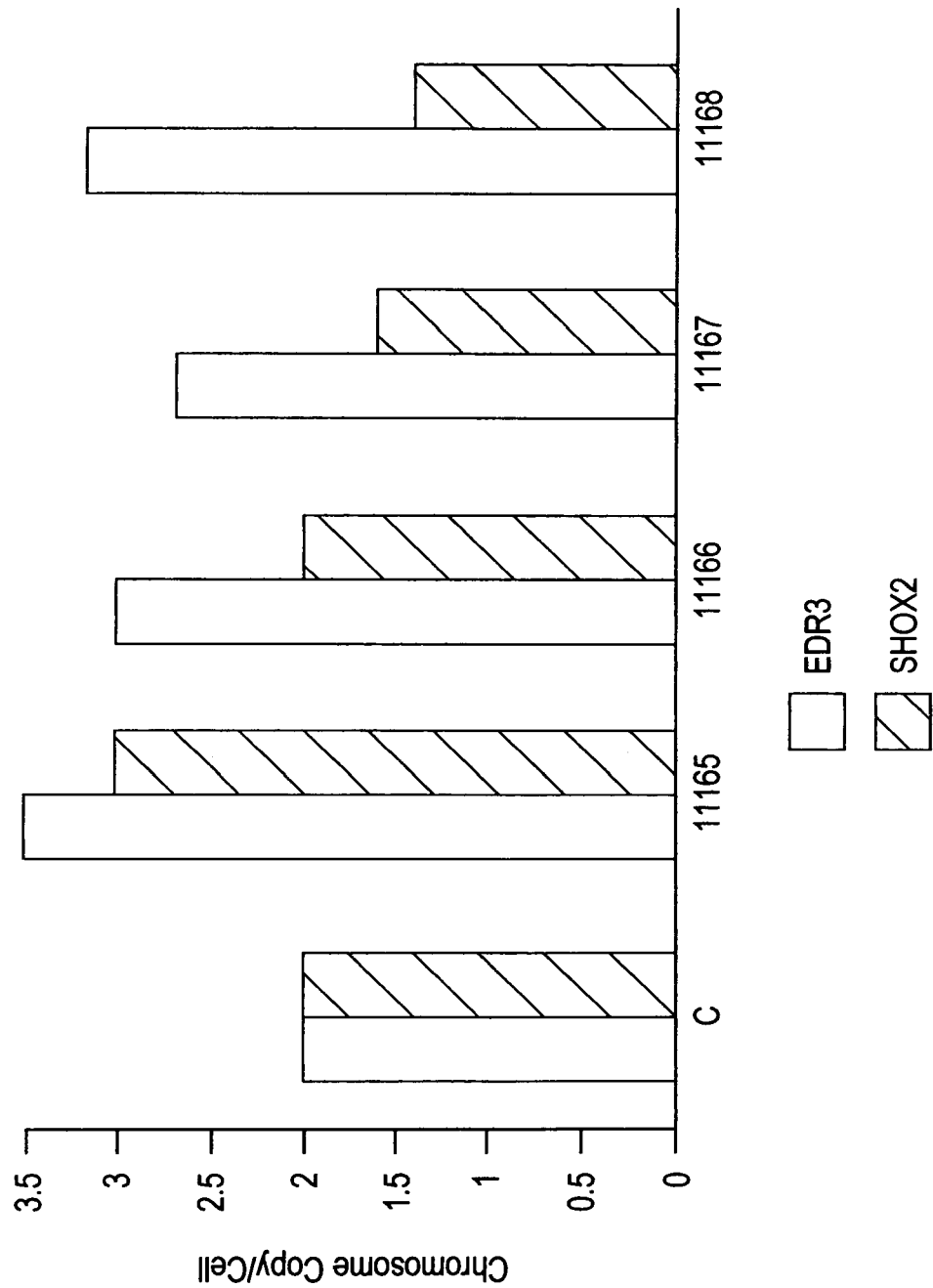

US 7,309,783 B2

MAMMALIAN EARLY DEVELOPMENTAL REGULATOR GENE

CROSS REFERENCE TO RELATED APPLICATIONS

This application claims priority from Provisional Application Ser. No. 60/289,767, filed May 9, 2001, which is incorporated herein by reference in its entirety.

STATEMENT REGARDING FEDERALLY SPONSORED RESEARCH

The U.S. Government has certain rights in this invention pursuant to Grant Nos. CA74802 and CA60122 awarded by the National Institute of Health.

TECHNICAL FIELD

This disclosure relates to the area of mammalian genes, and in particular to genes for the regulation of early development.

BACKGROUND OF DISCLOSURE

The Polycomb (PcG) superfamily of genes includes repressors of gene expression. PcG proteins form large, multimeric, chromatin-associated protein complexes that regulate genes, such as the homeotic genes involved in axial patterning, limb formation and other aspects of development. They may also be important in regulating cell growth and differentiation through regulation of the cell cycle, and have accordingly been targeted for use as therapeutic, prognostic, and diagnostic tools for proliferative and developmental disorders. There is accordingly a need for the identification of new genes in this family.

SUMMARY OF THE DISCLOSURE

Disclosed herein is an isolated polynucleotide selected from the group consisting of SEQ ID NO: 1, SEQ ID NO: 1 wherein T can also be U, nucleic acid sequences complementary to SEQ ID NO: 1, SEQ ID NO:3, SEQ ID NO:3 wherein T can also be U, nucleic acid sequences complementary to SEQ ID NO:3. Also disclosed is an expression vector comprising a polynucleotide selected from the group consisting of SEQ ID NO:1, SEQ ID NO:1 wherein T can also be U, and nucleic acid sequences complementary to SEQ ID NO:1, wherein the polynucleotide is operably linked to control sequences that direct transcription of the polynucleotide. Further disclosed is an isolated polynucleotide encoding an amino acid sequence as set forth in SEQ ID NO:2.

Also disclosed herein is a composition comprising an antibody that binds to a polypeptide of SEQ ID NO:2. The antibody can be polyclonal or monoclonal. Further disclosed is a method of producing an anti-EDR3 antibody comprising injecting an animal with a polypeptide comprising about 15 to about 30 contiguous amino acids of SEQ ID NO:2.

BRIEF DESCRIPTION OF THE DRAWINGS

Referring now to the figures, which are exemplary embodiments, and wherein the like elements are numbered alike:

FIG. 3 is a homology comparison of the proteins encoded by EDR3 (SEQ ID NO:2), EDR1 (SEQ ID NO:8), EDR2 (SEQ ID NO:9) and mouse Edr3 (SEQ ID NO:4);

FIG. 9 shows quantitative Southern analysis comparing edr3 to SHOX2 (another candidate gene located in 3q25-q26). The region of duplication is present in all four CsLS cases by Southern analysis.

DETAILED DESCRIPTION

The present disclosure relates to a novel mammalian regulator gene. More particularly, the disclosure relates to the novel mammalian early developmental regulator (edr3) gene and to its protein, both of which can be used, inter alia, as therapeutic and diagnostic tools for proliferative and developmental disorders and as vehicles for identifying region q26.2 on a mammalian chromosome 3.

The gene edr3 is located in the q26.2 region on chromosome 3 (q26.2). This region of chromosome 3 has been found in triplicate in humans having Cornelia de Lange syndrome (CdLs). CdLs is a genetic disorder that is characterized by certain craniofacial aspects (low anterior hairline, synophrys, antevered nares, maxillary prognathism, and long philtrum), together with prenatal and postnatal growth retardation, mental retardation, and in many cases upper limb abnormalities. CdLs is characterized by amplification of 3q26.2 such that the gene is overexpressed.

Figure 1:
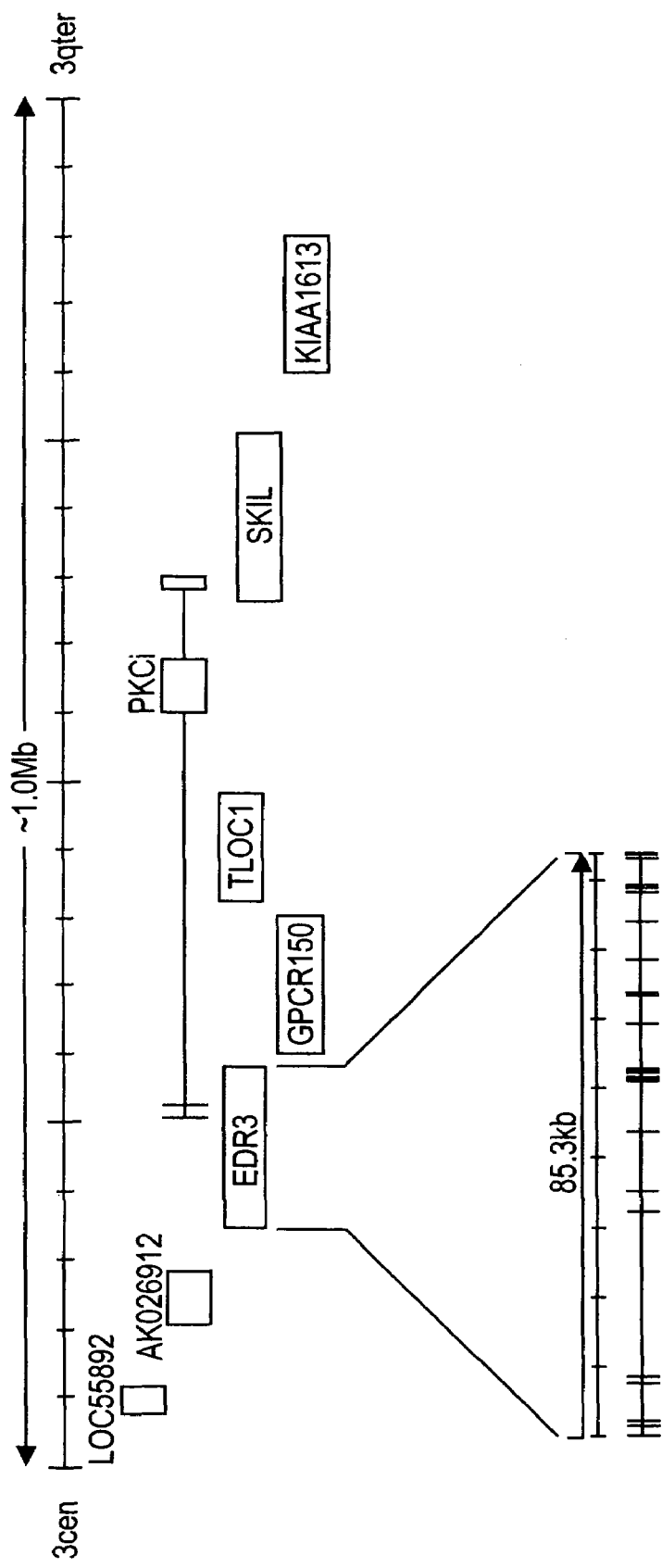
FIG. 1 is a schematic depicting the genomic region surrounding the edr3 gene on chromosome 3. The orientation of edr3 with regard to the centromere and other surrounding genes is shown.

The coding sequence of the edr3 gene comprises the nucleotide sequence shown in SEQ ID NO:1 as shown in FIG. 1. As used herein, the term "gene" means the segment of DNA involved in producing a polypeptide chain; it includes regions preceding and following the coding region (leader and trailer) as well as intervening sequences (introns) between individual coding segments (exons). FIG. 1 also depicts the amino acid sequence, SEQ ID NO:2, that correlates to SEQ ID NO:1. The edr3 gene comprises an open reading frame including about 2,895 base pairs organized into about 16 exons. The edr3 gene may comprise additional and/or alternative nucleotide sequences, such as, degenerate sequences, which encode the same amino acid sequences as shown in SEQ ID NO:2, truncated or deletion-containing sequences that do not affect biological function, and homologous sequences wherein the degree of homology, i.e., the degree of similarity in the nucleotide sequence, between SEQ ID NO:1 and the variant nucleotide sequence is about 0 to about 30%. Within this range, the variation is preferably about equal to or less than 20%, with about equal to or less than 10% more preferred.

Typically, homologous sequences can be confirmed by hybridization, wherein hybridization under stringent conditions as described, for example, in Sambrook et al., MOLECULAR CLONING: A LABORATORY MANUAL, 2d ed. (Cold Spring Harbor Press, Cold Spring Harbor, N.Y.) is preferred. Using the stringent hybridization outlined in Sambrook et al., (i.e., washing the nucleic acid fragments twice where each wash is at room temperature for 30 minutes with 2× sodium chloride and sodium citrate (SCC) and 0.1% sodium dodecyl sulfate (SDS); followed by washing one time at 50° C. for 30 minutes with 2×SCC and 0.1% SDS; and then washing two times where each wash is at room temperature for 10 minutes with 2×SCC), homologous sequences can be identified comprising at most about 25-30% base pair mismatches, with about 15-25% base pair mismatches preferred, and about 5-15% base pair mismatches more preferred.

The disclosure also provides an isolated polynucleotide sequence encoding the EDR3 polypeptide. By "isolated polynucleotide sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an automatically replicating plasmid or virus; or into the genomic DNA of a prokaryote or eukaryote, or which exists as a separate molecule (e.g., a cDNA) independent of other sequences. "Polynucleotide" or "nucleic acid sequence" refers to a polymeric form of nucleotides at least 5 bases in length. The nucleotides can be ribonucleotides, deoxyribonucleotides, or modified forms of either nucleotide. Modifications include but are not limited to known substitutions of a naturally-occurring base, sugar or internucleoside (backbone) linkage with a modified base such as 5-methylcytosine, a modified sugar such as 2'-methoxy and 2'-fluoro sugars, and modified backbones such as phosphorothioate and methyl phosphonate.

The polynucleotide can be a DNA molecule, a cDNA molecule, genomic DNA molecule, or an RNA molecule. The polynucleotide as DNA or RNA comprises a sequence wherein T can also be U. The polynucleotide can be complementary to SEQ ID NO:1, wherein complementary refers to the capacity for precise pairing between two nucleotides. For example, if a nucleotide at a certain position of a polynucleotide is capable of hydrogen bonding with a nucleotide at the same position in a DNA or RNA molecule, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process. As used herein, hybridization means hydrogen bonding, which may be Watson-Crick, Hoogsteen or reversed Hoogsteen hydrogen bonding, between complementary nucleoside or nucleotide bases.

In addition, polynucleotides that are substantially identical to SEQ ID NO:1 or which encode proteins substantially identical to SEQ ID NO:2 are included. By "substantially identical" is meant a polypeptide or polynucleotide having a sequence that is at least 85%, preferably 90%, and more preferably 95% or more identical to the sequence of the reference amino acid or nucleic acid sequence. For polypeptides, the length of the reference polypeptide sequence will generally be at least 16 amino acids, preferably at least 20 amino acids, more preferably at least 25 amino acids, and most preferably at least 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

Sequence identity and similarity can be measured using sequence analysis software (e.g., Sequence Analysis Software Package of the Genetics Computer Group, University of Wisconsin Biotechnology Center, 1710 University Avenue, Madison, Wis. 53705) with the default parameters specified therein.

The edr3 polynucleotides also include polynucleotides coding for polypeptide analogs, fragments or derivatives of antigenic polypeptides which differ from naturally-occurring edr3 forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptide) and which share some or all properties of naturally-occurring forms. These molecules include the incorporation of codons suitable for expression by selected non-mammalian hosts; the provision of sites for cleavage by restriction endonuclease enzymes; and the provision of additional initial, terminal or intermediate DNA sequences that facilitate construction of readily expressed vectors.

In addition, polynucleotides encoding all or a portion of the EDR3 protein are included, so long as they encode a polypeptide with EDR3 protein activity, such as axial alignment during development. Such polynucleotides include naturally occurring, synthetic and intentionally manipulated DNA molecules. For example, the edr3 polynucleotide may be subjected to site-directed mutagenesis by techniques known in the molecular biology art. There are 20 naturally occurring amino acids, most of which are specified by more than one codon. Therefore, degenerate nucleotide sequences are included as long as the EDR3 polypeptide encoded by the nucleotide sequence is functionally unchanged. Also included are polynucleotide sequences that encode amino acid sequences which differ from those of the edr3 gene, but which should not produce phenotypic changes.

The edr3 polynucleotide can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on Nickel columns. Such gene modification techniques and suitable additional sequences are well known in the molecular biology arts.

The edr3 polynucleotide can be inserted into a recombinant DNA vector for production of edr3 mRNA. Such vectors may be used for the in vitro or in vivo production of edr3 mRNA. For in vitro production of edr3 mRNA, the cDNA comprising SEQ ID NO:1, for example, is inserted into a plasmid containing a promoter for either SP6 or T7 RNA polymerase. The plasmid is cut with a restriction endonuclease to allow run-off transcription of the mRNA, and the RNA is produced by addition of the appropriate buffer, ribonucleotides, and polymerase. The RNA is isolated by conventional means such as ethanol precipitation. The mRNA can be capped or polyadenylated, for example, prior to injection into a cell such as a *Xenopus* oocyte.

The edr3 polynucleotide can be inserted into a recombinant expression vector. The term "recombinant expression vector" refers to a plasmid, virus, or other means known in the art that has been manipulated by insertion or incorporation of the edr3 genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The edr3 genetic sequence can be inserted into a vector adapted for expression in a bacterial, yeast, insect, amphibian, or mammalian cell that further comprises the regulatory elements necessary for expression of the nucleic acid molecule in the bacterial, yeast, insect, amphibian, or mammalian cell operatively linked to the nucleic acid molecule encoding EDR3. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., atg) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153: 516-544, 1987).

Examples of suitable bacteria are *E. coli* and *B.subtilis*. A preferred yeast vector is pRS426-Gal. Examples of suitable yeast are *Saccaromyces* and *Pichia*. Suitable amphibian cells are *Xenopus* cells. Suitable vectors for insect cell lines include baculovirus vectors. Rat or human cells are preferred mammalian cells.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., an EDR3 polypeptide), or fragment thereof.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of this disclosure, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*) or may be a mammalian cell, including a human cell.

Mammalian cell systems that utilize recombinant viruses or viral elements to direct expression may be engineered. For example, when using adenovirus expression vectors, the nucleic acid sequences encoding a foreign protein may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the EDR3 polypeptide in infected hosts (e.g., Logan & Shenk, *Proc. Natl. Acad. Sci. U.S.A.* 81:3655-3659, 1984).

For long-term, high-yield production of recombinant proteins, stable expression is preferred. Rather than using expression vectors that contain viral origins of replication, host cells can be transformed with the cDNA encoding an EDR3 fusion protein controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1 to 2 days in an enriched media, and then are switched to a selective media. A number of selection systems may be used, including but not limited to the herpes simplex virus thymidine kinase (Wigler et al., *Cell* 11: 233, 1977), hypoxanthine-guanine phosphoribosyltransferase (Szybalska & Szybalski, *Proc. Natl. Sci. U.S.A.* 48: 2026, 1962), and adenine phosphoribosyltransferase (Lowy et al., *Cell* 22: 817, 1980) genes can be employed in $t^k$, $hg^{prt}$ or $a^{prt}$ cells respectively.

In addition to the edr3 sequences described above, full-length edr3 cDNA, gene sequences or paralogs present in the same species or orthologs of the edr3 gene in other species can readily be identified without undue experimentation, by molecular biological techniques well known in the art. The identification of orthologs of edr3 can be useful for developing model animal systems more closely related to humans for use in drug design. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species, and "paralog" meaning a functionally similar sequence when considered within the same species.

Further disclosed herein is an isolated and purified protein of the edr3 gene. The isolated and purified EDR3 protein comprises the amino acid sequence shown in FIG. 1 and identified as SEQ ID NO:2. Any naturally occurring variants of this sequence that may occur in mammalian or human tissues and which have early developmental, tumor suppressive, or anti-proliferative activity are also within the scope of this disclosure. Thus, reference herein to either the nucleotide or amino acid sequence of EDR3 includes reference to naturally occurring variants of these sequences. Nonnaturally occurring variants that differ from SEQ ID NO:2 and retain biological function are also included herein. Preferably the variants comprise those proteins having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cystine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. This is especially true if the replacement does not involve an amino acid at an EDR3 protein binding site. Whether an amino acid change results in a functional peptide can readily be determined by assaying the properties of the EDR3 polypeptide derivative.

Mammalian polypeptides comprising equal to or about 22 to about all contiguous amino acids of the EDR3 amino acid sequence shown in SEQ ID NO:2 are also provided, with equal to or at least about 25 contiguous amino acids preferred, and equal to or at least about 30 amino acids more preferred. Both the glycosylated and unglycosylated forms of the EDR3 protein, and/or polypeptide derivatives thereof, may be used for producing EDR3 protein-specific monoclonal and/or polyclonal antibodies. As used herein, "polypeptide derivatives" include those polypeptides differing in length from a naturally-occurring EDR protein and comprising about five or more amino acids in the same primary order as is found in the EDR3 protein. Polypeptide molecules having substantially the same amino acid sequence as the EDR3 protein but possessing minor amino acid substitutions that do not substantially affect the ability of the EDR3 polypeptide derivatives to interact with EDR3-specific molecules, such as antibodies, are within the definition of EDR3 proteins. Polypeptide derivatives also include glycosylated forms, aggregative conjugates with other molecules and covalent conjugates with unrelated chemical moieties. Mammalian EDR3 proteins and polypeptides can be isolated and purified from, for example, human cells including cells such as such as thymus, testis, heart, prostate, ovary, small intestine, peripheral blood lymphocytes, skeletal muscle, pancreas, lung, liver, and kidney.

EDR3 proteins, polypeptides, or polypeptide derivatives can be purified by any method known in the art. These methods include, but are not limited to, size exclusion chromatography, ammonium sulfate fractionation, ion exchange chromatography, affinity chromatography, crystallization, electrofocusing, and preparative gel electrophoresis. Preferably, purification is according to any method known to those of ordinary skill in the art that will result in a preparation of edr3 protein or polypeptide substantially free from other proteins and from carbohydrates, lipids, or subcellular organelles. A preparation of isolated and purified edr3 protein is about 80 to about 100% pure, with at least about 90% purity preferred, at least about 95% purity more preferred, and at least about 99% especially preferred. Purity may be assessed by any means known in the art, such as SDS-polyacrylamide gel electrophoresis.

EDR3 proteins and polypeptides can also be produced by recombinant DNA methods or by synthetic chemical methods. For production of recombinant EDR3 proteins or polypeptides, edr3 coding sequences selected from the nucleotide sequence shown in FIG. 1 can be expressed in known prokaryotic or eukaryotic expression systems. Bacterial, yeast, insect, or mammalian expression systems can be used, as is known in the art. Synthetic chemical methods, such as solid phase peptide synthesis, can be used to synthesize edr3 proteins, polypeptides, or polypeptide derivatives.

Amino acids essential for the function of EDR3 polypeptides can be identified according to procedures known in the art, such as site-directed mutagenesis or alanine-scanning mutagenesis (Cunningham and Wells, *Science* 244: 1081-1085, 1989; Bass et al., *Proc. Natl. Acad. Sci. USA* 88: 4498-4502, 1991). In the latter technique, single alanine mutations are introduced at different residues in the molecule, and the resultant mutant molecules are tested for biological activity (e.g., ligand binding and signal transduction) to identify amino acid residues that are critical to the activity of the molecule. Sites of ligand-protein interaction can also be determined by analysis of crystal structure as determined by such techniques as nuclear magnetic resonance, crystallography or photoaffinity labeling. (See, for example, de Vos et al., *Science* 255: 306-312, 1992; Smith et al., *J. Mol. Biol.* 224: 899-904, 1992; Wlodaver et al., *FEBS Lett.* 309: 59-64, 1992). The identities of essential amino acids can also be inferred from analysis of homologies with related proteins.

Multiple amino acid substitutions can be made and tested using known methods of mutagenesis and screening, such as those disclosed by Reidhaar-Olson and Sauer, *Science* 241: 53-57, 1988; or Bowie and Sauer, *Proc. Natl. Acad. Sci. USA* 86: 2152-2156, 1989. Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30: 10832-10837, 1991; Ladner et al., U.S. Pat. No. 5,223,409; Huse, WIPO Publication WO 92/06204) and region-directed mutagenesis (Derbyshire et al., *Gene* 46: 145, 1986; Ner et al., *DNA* 7: 127, 1988).

Mutagenesis methods as disclosed above can be combined with high-throughput screening methods to detect the activity of cloned, mutagenized proteins in host cells. Mutagenized DNA molecules that encode active proteins or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

It has been discovered herein that edr3, a novel polycomb gene family member is consistently located within the region of duplication in CDLS patients, including patients with apparently normal karyotypes. Importantly, analysis in mouse embryos reveals Edr3 expression in the principal target tissues for CDLS. Because PcG genes have been implicated in axial skeleton patterning and have been shown to be sensitive to dosage effects in transgenic mice, our data suggest that the EDR3 gene as a strong candidate for the CDLS locus. This is the first report of a PcG gene duplication leading to dysmorphology in humans.

There are approximately 1000 families with children that have CdLs. CdLs occurs in the population with a frequency of about 1 in 30,000 live births. In one embodiment, the edr3 polynucleotide can be used in genetic testing for an edr3 gene duplication in families where there is evidence of CdLs inheritance. Edr3 polynucleotides and fragments thereof can be used as a part of a diagnostic test kit for identifying cells or tissues that express a drug-metabolizing enzyme protein, such as by measuring a level of an edr3 nucleic acid in a sample of cells from a subject e.g., mRNA or genomic DNA, or determining if an edr3 gene has been mutated. Alternatively, an increase in the level of edr3 mRNA in a cell compared to normal controls can indicate the presence of a disorder such as CdLs in which there has been a gene duplication. Other methods such as FISH, PCR, Northern blots, Southern blots and other tests that can detect either the level of mRNA or the presence of a gene duplication can be used in a test for CdLs syndrome.

Unlike the overexpression of the edr3 gene in CdLs patients, underexpression or loss of the edr3 gene is implicated in neoplastic disorders. Neoplasias include, but are not limited to, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, tumors of mixed origin, such as Wilms' tumor and teratocarcinomas, and metastatic tumors. In particular, edr3 may act as a tumor suppressor gene in neoplastic diseases such as osteosarcoma and chondrosarcoma. Furthermore, while not wanting to be bound by any theory, it is believed that mutations of edr3 are involved in the formation and/or the development of neoplasias and other proliferative disorders. Due to the implications of both the overexpression and the underexpression of the edr3 gene, methods for regulating the expression of the edr3 gene, along with methods for regulating the presence of edr3 nucleotides and proteins, have therapeutic value.

In one embodiment, the edr3 polynucleotide can be used in somatic gene therapy applications. Somatic gene therapy can be defined as the ability to program the expression of foreign genes in non-germ line (i.e., non-sperm and egg) cells of an animal or patient. Recent advances in molecular biology including the cloning of many human genes and the development of viral and chemical gene delivery systems have brought us to the threshold of somatic gene therapy. All methods of gene therapy can be divided into two categories: ex vivo and in vivo. Ex vivo gene therapy involves the removal of cells from a host organism, introduction of a foreign gene into those cells in the laboratory, and reimplantation or transplantation of the genetically modified cells back into a recipient host.

In contrast, in vivo gene therapy involves the introduction of a foreign gene directly into cells of a recipient host without the need for prior removal of those cells from the organism. In vivo gene therapy can make use of infectious vectors such as retroviral vectors that include the edr3 polynucleotide or a fragment thereof.

There are a number of requirements that must be met by any method of gene therapy before it can be considered potentially useful for human therapeutics. First, one must develop an efficient method for introducing the foreign gene into the appropriate host cell. Secondly, it would be preferable to develop systems that program expression of the gene only in the appropriate host cell type, thus preventing expression of the foreign gene in an inappropriate cell. Finally, and most importantly when considering human gene therapy, the technique must have a minimal risk of mutating the host cells and of causing a persistent infection of the host organism, a particularly important worry when using virus vectors to introduce foreign genes into host cells. Somatic gene therapy is described in detail in Ledley, F., Human Gene Therapy 2: 77-83, (1991) and Ledley, F., Pharmaceutical Research, vol. 13: 1595-1613, November (1996).

Therefore, the present disclosure contemplates a method for gene therapy using the edr3 polynucleotide. One embodiment includes forming a homologously recombinant cell comprising a DNA construct comprising all or part of the edr3 gene sequence of FIG. 1. A method for forming such a construct, for example, may be found in U.S. Pat. No. 5,641,670 which is incorporated in its entirety herein by reference. The regulation or activity of endogenous genes of interest in a cell can be altered by inserting into the cell genome, at a preselected site, through homologous recombination, DNA constructs comprising: (a) a targeting sequence; (b) a regulatory sequence; (c) an exon and (d) an unpaired splice-donor site, wherein the targeting sequence directs the integration of elements (a)-(d) such that the elements (b)-(d) are operatively linked to the endogenous gene. Alternatively, the DNA constructs may comprise: (a)

a targeting sequence, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the first exon of the endogenous gene. The targeting sequences used are preferably selected with reference to the site into which the DNA is to be inserted. In both embodiments the targeting event is used to create a new transcription unit, which is a fusion product of sequences introduced by the targeting DNA constructs and the endogenous cellular gene. As discussed herein, for example, the formation of the new transcription unit allows transcriptionally silent genes (genes not expressed in a cell prior to transfection) to be activated in host cells by introducing into the host cell's genome DNA constructs as disclosed herein. As also discussed herein, the expression of an endogenous gene which is expressed in a cell as obtained can be altered in that it is increased, reduced, including eliminated, or the pattern of regulation or induction may be changed through use of the method and DNA constructs of the present invention.

The targeting sequence or sequences are DNA sequences which permit legitimate homologous recombination into the genome of the selected cell containing the gene of interest. Targeting sequences are, generally, DNA sequences which are homologous to (i.e., identical or sufficiently similar to cellular DNA such that the targeting sequence and cellular DNA can undergo homologous recombination) DNA sequences normally present in the genome of the cells as obtained (e.g., coding or noncoding DNA, lying upstream of the transcriptional start site, within, or downstream of the transcriptional stop site of a gene of interest, or sequences present in the genome through a previous modification). The targeting sequence or sequences used are selected with reference to the site into which the DNA in the DNA construct is to be inserted.

In another embodiment, an EDR3 fusion protein is provided. These mammalian fusion proteins are useful for generating antibodies against EDR3 amino acid sequences and for use in various assay systems. Therefore, the mammalian fusion proteins may be used, for example, to detect EDR3 expression and to provide a defense mechanism for EDR3 expression when desired. For example, EDR3 fusion proteins can be used to identify proteins that interact with the EDR3 protein and influence its function. This interaction may impart specificity to the ability of EDR3 to regulate other proteins, or it may increase or decrease the effect of EDR3 function. Identification of proteins that interact with EDR3 may provide a target for novel drugs. Physical methods, such as protein affinity chromatography, or library-based assays for protein-protein interactions, such as the yeast two-hybrid or phage display systems, can be used for this purpose. Such methods are well known in the art, and can be used, inter alia, as drug screens.

An EDR3 fusion protein comprises at least two protein segments fused together by means of a peptide bond. The first protein segment can comprise in whole or in part the contiguous amino acids of an EDR3 protein. Where in part, at least about 8 contiguous amino acids of the EDR3 protein are used, with at least about 10 preferred, at least about 15 more preferred, and at least about 20 especially preferred. The amino acids can be selected from the amino acid sequence shown in FIG. 1, or from a naturally or nonnaturally occurring, biologically active variant of that sequence. The first protein segment can also be a full-length EDR3 protein. The second protein segment can comprise a full-length protein or a protein fragment or polypeptide that may or may not be derived from EDR3. The second protein segment can comprise an enzyme, which will generate a detectable product, such as beta-galactosidase or other enzymes that are known in the art. Alternatively, the second protein segment can include a fluorescent protein such as green fluorescent protein or other fluorescent proteins known in the art. Additionally, the fusion protein can be labeled with a detectable marker, such as a radioactive maker, a fluorescent marker, a chemilluminescent marker, a biotinylated marker, and the like.

Techniques for making fusion proteins, either recombinantly or by covalently linking two protein segments are well known. Recombinant DNA methods can be used to construct EDR3 fusion proteins, for example, by making a DNA construct that comprises EDR3 coding sequences selected from FIG. 1 in proper reading frame with nucleotides encoding the second protein segment and expressing the DNA construct in a host cell, as described below.

In yet another embodiment, an expression construct for expressing all or a portion of a mammalian EDR3 protein is provided, wherein the expression construct comprises a polynucleotide segment located downstream from a promoter wherein the promoter serves as the initiation site for the transcription of the polynucleotide segment. The polynucleotide segment comprises polynucleotides that encode all or a part of a mammalian EDR3 protein. Where the polynucleotide segment comprises a part of the mammalian EDR3 protein, the polynucleotide segment includes at least about 8 contiguous amino acids of a mammalian EDR3 protein, with at least about 15 preferred, and at least about 20 more preferred. The promoter used in forming the construct may be selected from a variety of promoters available in the art; however, the promoters selected are preferably functional in the particular host cell in which the polynucleotide segment is to be expressed. Such a promoter may be selected from a large number of cell type-specific promoters known and used in the art.

The expression construct can also comprise a transcription terminator that is functional in the host cell. The expression construct can be linear or circular and can comprise sequences for autonomous replication.

The expression construct may be expressed in a prokaryotic or eukaryotic host cell, which may include, for example, bacterial, yeast, insect, and human cells. The expression constructs can be introduced into the host cells using techniques such as, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, calcium phosphate-mediated transfection, and the like.

In another embodiment, antibodies that specifically bind to all or a part of the EDR3 protein are provided. Isolated and purified EDR3 proteins, polypeptides, or fusion proteins can be used as immunogens, to obtain a preparation of antibodies, which specifically bind to an EDR3 protein. The antibodies can be used to detect wild-type EDR3 proteins in mammalian tissue, and in particular, in human tissue. The antibodies can also be used to detect the presence of mutations in the edr3 gene which results in overexpression of the EDR3 protein or in EDR3 proteins with altered size or electrophoretic mobilities.

Preparations of polyclonal and monoclonal EDR3 antibodies can be made using standard methods known in the art. The antibodies can specifically bind to epitopes present in EDR3 proteins having the amino acid sequence shown in FIG. 1. As used herein, "epitope" is defined as a molecular region on the surface of an EDR3 protein, which is capable of eliciting an immune response and of combining with a specific antibody. Preferably, antibodies that specifically bind to the epitopes of EDR3 proteins do not detect other proteins in immunochemical assays and can immunoprecipitate EDR3 proteins from solution. Preferably, the EDR3 epitopes are not present in other mammalian proteins. The epitope may be formed by all or part of the EDR3 protein. However, where contiguous amino acids, i.e., consecutive amino acids that are connected to each other in an unbroken sequence, are used to form the epitope, at least about 6 amino acids may be used, with about 8 preferred, about 10 more preferred, and about 12 especially preferred. Where non-contiguous amino acids, i.e., consecutive amino acids having at least one amino acid connected to another amino acid by intervening non-essential amino acids, are used to form the epitope, at least about 15 amino acids may be used, with about 25 amino acids preferred, and about 50 amino acids more preferred. Antibodies that specifically bind to edr3 proteins provide a detection signal of greater than about 30 times that of detection signals found with other proteins as determined by Western blots or other immunochemical assays. Such specific antibodies may provide a detection signal of at least about 5 times the detection signal obtained from other proteins, with at least about 10 times preferred, and at least about 20 times more preferred.

The present disclosure includes isolated (i.e., removed from their natural milieu) antibodies that selectively bind EDR3 or a mimetope thereof. As used herein, the term "selectively binds to" refers to the ability of antibodies of the present disclosure to preferentially bind to EDR3 and mimetopes thereof. Binding can be measured using a variety of methods standard in the art including enzyme immunoassays (e.g., ELISA), immunoblot assays, etc.; see, for example, Sambrook et al., Eds., *Molecular Cloning: A Laboratory Manual*, 2nd ed., Cold Spring Harbor Laboratory Press, 1989, or Harlow and Lane, Eds., *Using Antibodies*, Cold Spring Harbor Laboratory Press, Pages 269-309, 1999.

Isolated antibodies of the present disclosure can include antibodies in serum, or antibodies that have been purified to varying degrees. Such antibodies may be polyclonal antibodies, monoclonal antibodies, humanized or chimeric antibodies, anti-idiotypic antibodies, single chain antibodies, Fab fragments, fragments produced from an Fab expression library, and epitope-binding fragments of the above.

Antibodies that bind to ER3 can be prepared from the intact polypeptide or fragments containing peptides of interest as the immunizing agent. The preparation of polyclonal antibodies is well known in the molecular biology art; see for example, *Production of Polyclonal Antisera in Immunochemical Processes* (Manson, ed.), pages 1-5 (Humana Press 1992) and Coligan et al., *Production of polyclonal Antisera in Rabbits, Rats, Mice and Hamsters in Current Protocols in Immunology*, section 2.4.1 (1992).

A monoclonal antibody composition can be antibodies produced by clones of a single cell called a hybridoma that secretes or otherwise produces one kind of antibody molecule. Hybridoma cells can be formed by fusing an antibody-producing cell and a myeloma cell or other self-perpetuating cell line. The preparation of monoclonal antibodies was first described by Kohler and Milstein, Nature 256, 495-497 (1975), although numerous variations have been described for producing hybridoma cells.

Briefly, monoclonal antibodies can be obtained by injecting mammals such as mice or rabbits with a composition comprising an antigen, thereby inducing in the animal antibodies having specificity for the antigen. A suspension of antibody-producing cells is then prepared (e.g., by removing the spleen and separating individual spleen cells by methods known in the art). The antibody-producing cells are treated with a transforming agent capable of producing a transformed or "immortalized" cell line. Transforming agents are known in the art and include such agents as DNA viruses (e.g., Epstein Bar Virus, SV40), RNA viruses (e.g., Moloney Murine Leukemia Virus, Rous Sarcoma Virus), myeloma cells (e.g., P3X63-Ag8.653, Sp2/0-Ag14) and the like. Treatment with the transforming agent can result in production of a hybridoma by means of fusing the suspended spleen cells with, for example, mouse myeloma cells. The transformed cells are then cloned, preferably to monoclonality. The cloning is preferably performed in a medium that will not support non-transformed cells, but that will support transformed cells. The tissue culture medium of the cloned hybridoma is then assayed to detect the presence of secreted antibody molecules by antibody screening methods known in the art. The desired clonal cell lines are then selected.

A therapeutically useful anti-EDR3 antibody may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., *Nature* 321: 522, 1986 and Singer et al., *J. Immunol.* 150: 2844, 1993. The antibodies can also be derived from human antibody fragments isolated from a combinatorial immunoglobulin library; see, for example, Barbas et al., *Methods: A Companion to Methods in Enzymology* 2, 119, 1991.

In addition, chimeric antibodies can be obtained by splicing the genes from a mouse antibody molecule with appropriate antigen specificity together with genes from a human antibody molecule of appropriate biological specificity; see, for example, Takeda et al., *Nature* 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies against EDR3, as described, for example, in U.S. Pat. No. 4,946,778. Single chain antibodies are formed by linking the heavy and light chain fragments of the Fv region via an amino acid bridge, resulting in a single chain polypeptide.

Antibody fragments that recognize specific epitopes can be generated by techniques well known in the art. Such fragments include Fab fragments produced by proteolytic digestion, and Fab fragments generated by reducing disulfide bridges.

When used for immunotherapy, the monoclonal antibodies, fragments thereof, or both, that bind to EDR3 may be unlabelled or labeled with a therapeutic agent. These agents can be coupled directly or indirectly to the monoclonal antibody by techniques well known in the art, and include such agents as drugs, radioisotopes, lectins and toxins.

In another method, EDR3 antibodies of the present disclosure can be produced recombinantly using techniques known in the art. Recombinant DNA methods for producing antibodies include isolating, manipulating, and expressing the nucleic acid that codes for all or part of an immunoglobulin variable region including both the portion of the variable region comprised by the variable region of the immunoglobulin light chain and the portion of the variable region comprised by the variable region of the immunoglobulin heavy chain. Methods for isolating, manipulating and expressing the variable region coding nucleic acid in eukaryotic and prokaryotic hosts are disclosed in U.S. Pat. No. 4,714,681; Sorge et al. Mol. Cell. Biol. 4, 1730-1737 (1984); Beher et al. Science 240, 1041-1043 (1988); Skerra et al., Science 240, 1030-1041 (1988); and Orlandi et al. Proc. Natl. Acad. Sci. U.S.A. 86, 3833-3837 (1989).

Antibodies raised against EDR3 or mimetopes can be advantageous because such antibodies are not substantially contaminated with antibodies against other substances that might otherwise cause interference in a diagnostic assay or side effects if used in a therapeutic composition.

A preferred method to produce EDR3 antibodies includes (a) administering to an animal an effective amount of EDR3 (ranging in size from a peptide to a full-length protein) or mimetope thereof to produce the antibodies and (b) recovering the antibodies.

Antibodies can be purified by methods known in the art. Suitable methods for antibody purification include purification on a Protein A or Protein G beads, protein chromatography methods (e.g., DEAE ion exchange chromatography, ammonium sulfate precipitation), antigen affinity chromatography and others.

As used herein "EDR3 antibody" refers to an antibody capable of complexing with EDR3.

In another embodiment, a method of identifying the neoplastic tissue of a mammal or human is provided. The method comprises comparing the expression of an edr3 gene in a first tissue of a mammal suspected of being neoplastic with the expression of an edr3 gene in a second tissue of a non-neoplastic mammal. Overexpression or physical or molecular alteration of the edr3 gene in the first tissue identifies the first tissue as being neoplastic. The tissue suspected of being neoplastic can be derived from a different mammalian tissue type, but preferably it is derived from the same tissue type, for example an intestinal polyp or other abnormal growth. A difference between the edr3 gene, mRNA, or protein in the two tissues which are compared, for example in molecular weight, amino acid or nucleotide sequence, or relative abundance, indicates a somatic mutation in the edr3 gene (or a gene which regulates it) in the tissue of the mammal which was suspected of being neoplastic.

The edr3 genes in the two tissues can be compared by any means known in the art. For example, the two genes can be sequenced, and the sequence of the edr3 gene in the tissue suspected of being neoplastic can be compared with the wild-type sequence in the normal tissue. The edr3 genes or portions of the edr3 genes in the two tissues can be amplified using the polymerase chain reaction (PCR), for example using nucleotide primers selected from the nucleotide sequence shown in FIG. 1. The amplified genes or portions of genes can be hybridized to nucleotide probes selected from the nucleotide sequence shown in FIG. 1. The nucleotide probes can be labeled by a variety of methods, such as radiolabeling, biotinylation, or labeling with fluorescent or chemiluminescent tags, and detected by standard methods known in the art.

Alternatively, edr3 mRNA in the two tissues can be compared. PolyA+RNA can be isolated from the two tissues as is known in the art. For example, one of skill in the art can readily determine differences in the size or amount of edr3 mRNA transcripts between the two tissues that are compared, using Northern blots, ribonucleotide protection asay (RPA) and nucleotide probes selected from the nucleotide sequence shown in FIG. 1. Alteration in the size, quantity or expression of edr3 mRNA in a tissue sample suspected of being neoplastic compared with the expression of edr3 mRNA in a normal tissue is indicative of neoplasia.

Any method for analyzing proteins can be used to compare two EDR3 proteins from matched samples. The sizes of the EDR3 proteins in the two tissues can be compared, for example, using the antibodies of the present invention to detect EDR3 proteins in Western blots of protein extracts from the two tissues. Other changes, such as expression levels and subcellular localization, can also be detected immunologically. A higher EDR3 protein expression level in a tissue suspected of being neoplastic compared with the EDR3 protein expression level in a normal tissue is indicative of neoplasia.

In another embodiment, a method to aid in the diagnosis or prognosis of neoplasia in a mammal is provided. Thus, comparison of edr3 gene sequences or of edr3 gene expression products, e.g., mRNA and protein, between a tissue of a mammal which is suspected of being neoplastic and a normal tissue of a mammal can be used to diagnose or prognose neoplasia in the mammal. Such comparisons of edr3 genes, mRNA, or protein can be made as described above. Overexpression of the edr3 gene in the tissue suspected of being neoplastic indicates neoplasia in the tissue. The degree of overexpression of the edr3 gene in the neoplastic tissue relative to wild-type expression of the gene in normal tissue, or differences in the amount of overexpression of the edr3 gene in the neoplastic tissue over time, can be used to prognose the progression of the neoplasia in that tissue or to monitor the response of the neoplastic tissue to various therapeutic regimens over time.

In another embodiment, a method to aid in detecting a genetic predisposition to neoplasia in a mammal is provided. Fetal tissues that can be used for this purpose include, but are not limited to, amniotic fluid, chorionic villi, blood, the blastomere of an in vitro-fertilized embryo, and the like. The wild-type edr3 gene can be obtained from any tissue. The mRNA or protein can be obtained from a normal tissue of a human in which the edr3 gene is expressed. Such tissues are disclosed above. Differences such as alterations in the nucleotide sequence or size of the fetal edr3 gene or mRNA, or alterations in the molecular weight, amino acid sequence, or relative abundance of fetal edr3 protein indicate a germline mutation in the edr3 gene of the fetus that indicates a genetic predisposition to neoplasia. The amounts of the edr3 gene, mRNA or protein can be quantified using any of the methods described above. The alterations in DNA sequences can be identified using nucleotide primers for the edr3 gene and a second unrelated control set of primers from a gene with a known expression pattern in a quantitative PCR reaction and comparing the relative ratios of the two PCR products.

Another embodiment provides a method for inducing a cell to change its pattern of differentiation, for example, in order to study the process of oncogenesis and test compounds which affect this process. The method comprises contacting a cell with an effective amount of all or a portion of a mammalian or human edr3 gene or expression product capable of inducing the cell to change its pattern of differentiation. The cell contacted can include any mammalian cell which expresses the edr3 gene, including, but not limited to, bone, thymus, testis, heart, prostate, ovary, small intestine, peripheral blood lymphocytes, skeletal muscle, pancreas, lung, liver, kidney, and the like.

In another embodiment, expression of an endogenous edr3 gene in a cell can be altered by introducing a DNA construct in frame with the endogenous edr3 gene. The DNA construct may comprise a targeting sequence, a regulatory sequence, an exon, and an unpaired splice donor site. Such an alteration may occur by homologous recombination, such that a homologously recombinant cell comprising the DNA construct is formed. This method of affecting endogenous gene expression is taught in U.S. Pat. No. 5,641,670, which is incorporated herein in its entirety by reference.

The targeting sequence may comprise the nucleotide sequence shown in FIG. 1 in whole or in part. Where in part, at least about 10 contiguous nucleotides from the nucleotide sequence shown in FIG. 1 are used, with at least about 12 preferred, at least about 15 more preferred, at least about 20 even more preferred, and at least about 50 especially preferred. The transcription unit is located upstream to a coding sequence of the endogenous edr3 gene. The exogenous regulatory sequence directs transcription of the coding sequence of the edr3 gene. Preferably, the homologously recombinant cell is a differentiated cell. In addition, it is preferred that the exogenous regulatory sequence directs decreased transcription of the coding sequence of the edr3 gene.

In yet another embodiment, an isolated and purified subgenomic polynucleotide comprising EDR3 is provided. As used herein, the subgenomic polynucleotide includes polynucleotides having fewer nucleotides than are contained on the chromosome. The isolated and purified subgenomic polynucleotide may comprise about 10 to about 2951 contiguous nucleotides selected from the nucleotide sequence shown in FIG. 1, with at least equal to or about 18 contiguous nucleotides preferred, with at least equal to or about 30 contiguous nucleotides more preferred. Preferably, the polynucleotides are intron-free. Purified and isolated EDR3 subgenomic polynucleotides can be used, inter alia, as primers to obtain additional copies of the polynucleotides, to express edr3 mRNA, protein, polypeptides, or fusion proteins, and as probes for identifying wild-type and mutant EDR3 coding sequences. The probes can also be used to identify the mammalian chromosome 3.

Subgenomic edr3 polynucleotides can be isolated and purified free from other nucleotide sequences using standard nucleic acid purification techniques. For example, restriction enzymes and probes can be used to isolate polynucleotide fragments that comprise the edr3 coding sequences. Isolated polynucleotides may be in preparations that are about 80% to about 100% free of other molecules, with greater than about 85% purity preferred, and greater than about 90% more preferred.

Complementary DNA encoding edr3 proteins can be made using reverse transcriptase, with edr3 MRNA as a template. The polymerase chain reaction (PCR) can be used to obtain the polynucleotides, using either human genomic DNA or cDNA as a template. Alternatively, synthetic chemistry techniques can be used to synthesize the polynucleotide molecules of the invention. The degeneracy of the genetic code allows alternate nucleotide sequences to be synthesized that will encode an edr3 protein having the amino acid sequence shown in FIG. 1. All such nucleotide sequences are within the scope of the present disclosure.

As the edr3 gene maps to human chromosome region 3q26.2, an eleventh embodiment includes a method for identifying region q26.2 on chromosome 3 is provided. The method comprises contacting prepared metaphase mammalian, i.e., human, chromosomes with a nucleotide probe having at least, in whole or in part, the nucleotide sequence shown in FIG. 1, and detecting a region of a chromosome that specifically hybridizes to the nucleotide probe. A region of a chromosome that specifically hybridizes to the nucleotide probe includes a q26.2 region of chromosome 3.

Preparations of human metaphase chromosomes can be prepared using standard cytogenetic techniques from human primary tissues or cell lines. Nucleotide probes comprising at least 12 contiguous nucleotides selected from the nucleotide sequence shown in FIG. 1 may be used to identify the human chromosome. The nucleotide probes can be labeled, for example, with a radioactive, fluorescent, biotinylated, or chemiluminescent label, and detected by well-known methods appropriate for the particular label selected. Protocols for hybridizing nucleotide probes to preparations of metaphase chromosomes are well known in the art. A nucleotide probe will hybridize specifically to nucleotide sequences in the chromosome preparations that are complementary to the nucleotide sequence of the probe. A probe that hybridizes specifically to human chromosome region 3q26.2 hybridizes to nucleotide sequences present in the edr3 gene and not to nucleotide sequences present in other human genes. A probe that hybridizes specifically to an edr3 gene provides a detection signal of at least 5, 10- or 20-fold higher than the background hybridization provided with non-edr3 coding sequences.

In another embodiment, cells transformed with wild-type edr3 subgenomic polynucleotides can be used to study oncogenesis and drug treatments effective in preventing transformation to an oncogenic phenotype. Oncogenesis is a process that involves alterations in gene expression in the transformed cells. These alterations in gene expression are reflected in morphological and biochemical changes in the transformed cells. Morphological changes can be studied, for example, by observing the transformed cells microscopically and comparing the appearance of the transformed cells with cells that have not received a wild-type edr3 gene. Biochemical alterations can be studied, inter alia, by comparing the proteins which are expressed by the cells before and at various times after transformation with the wild-type edr3 gene. Methods of comparing proteins between two cells, such as using SDS polyacrylamide electrophoresis, are well known in the art. Cells transformed with a wild-type edr3 gene and in the process of becoming neoplastic can also be exposed to various drug treatments to determine which treatments promote the morphological or biochemical changes which accompany acquisition of the neoplastic phenotype.

Similarly, cells transformed with wild-type edr3 subgenomic polynucleotides can also be used to study changes that accompany cellular differentiation in progenitor cells and responses of these cells to test compounds that affect differentiation. Expression of an endogenous edr3 gene in a cell can be altered by introducing in frame with the endogenous edr3 gene a DNA construct comprising an edr3 targeting sequence, a regulatory sequence, an exon, and an unpaired splice donor site by homologous recombination, such that a homologously recombinant cell comprising the DNA construct is formed. The new transcription unit can be used to turn the edr3 gene on or off as desired. This method of affecting endogenous gene expression is taught in U.S. Pat. No. 5,641,670, which is incorporated herein by reference in its entirety.

In another embodiment, a therapeutic composition is formed comprising polynucleotides, antisense or sense, of the edr3 gene. As used herein, antisense polynucleotides are those nucleotides that serve as the template for mRNA synthesis. The therapeutic composition can inhibit edr3 gene expression by blocking and/or decreasing expression of the edr3 gene. The therapeutic composition can comprise the antisense strand of all or a portion of the human edr3 gene in a pharmaceutically acceptable carrier. The edr3 antisense product can be, e.g., mRNA or DNA. The cell to be treated can comprise any mammalian capable of expressing the edr3 gene. The therapeutic composition can comprise an oligonucleotide comprising a sense or antisense fragment of the edr3 polynucleotide.

Oligonucleotide agents for the modulation of edr3 gene expression can be nucleic acid molecules substantially complementary to an edr3 gene. Such approaches include oligonucleotide-based therapies such as antisense, ribozymes, triple helices and double stranded interfering RNAs.

Oligonucleotides may be designed to reduce or inhibit mutant target gene activity. Techniques for the production and use of such molecules are well known to those of ordinary skill in the art. Antisense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred. Antisense oligonucleotides are preferably 10 to 50 nucleotides in length, and more preferably 15 to 30 nucleotides in length. An antisense compound is an antisense molecule corresponding to the entire edr3 mRNA or a fragment thereof.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules includes one or more sequences complementary to the target gene mRNA, and includes the well known catalytic sequence responsible for mRNA cleavage disclosed, for example, in U.S. Pat. No. 5,093,246. Within the scope of this disclosure are engineered hammerhead motif ribozyme molecules that specifically and efficiently catalyze endonucleolytic cleavage of RNA sequences encoding target gene proteins. Specific ribozyme cleavage sites within any potential RNA target are initially identified by scanning the molecule of interest for ribozyme cleavage sites that include the sequences GUA, GUU, and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules used in triple helix formation for the inhibition of transcription should be single stranded and composed of deoxyribonucleotides. The base composition of these oligonucleotides are designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences targeted for triple helix formation may be increased by creating a "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Double stranded interfering RNA molecules are also useful; see, for example, Fire et al., *Nature* 391: 860-11, 1998. Such molecules interfere with the expression of a target gene. For example, double stranded RNA molecules can be injected into a target cell or organism to inhibit expression of a target gene and thus the activity of the gene product. Such double stranded RNA molecules can be more effective at inhibiting gene expression than either strand alone.

The antisense, ribozyme, triple helix and/or double stranded interfering RNA molecules described herein may reduce or inhibit the transcription (triple helix) and/or translation (antisense, ribozyme, double stranded interfering RNAs) of mRNA produced by both normal and mutant target gene alleles. If it is desired to retain substantially normal levels of target gene activity, nucleic acid molecules that encode and express target gene polypeptides exhibiting normal activity may be introduced into cells via gene therapy methods that do not contain sequences susceptible to whatever antisense, ribozyme, or triple helix treatments are being utilized. Alternatively, it may be preferable to coadminister normal target gene protein into the cell or tissue in order to maintain the requisite level of cellular or tissue target gene activity.

Antisense RNA and DNA, ribozyme, and triple helix molecules may be prepared by any method known in the art for the synthesis of DNA and RNA molecules. These include techniques for chemically synthesizing oligodeoxyribonucleotides and oligoribonucleotides, for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Various well-known modifications to the DNA molecules may be introduced as a means of increasing intracellular stability and half-life. Possible modifications include but are not limited to the addition of flanking sequences of ribonucleotides or deoxyribonucleotides of the 5' and/or 3' ends of the molecule or the use of phosphorothioate or 2' O-methyl rather than phosphodiesterase linkages within the oligodeoxyribonucleotide backbone.

Modulators of edr3 expression are identified in a method wherein a cell is contacted with a candidate compound and the expression of edr3 mRNA or protein in the cell is determined. The level of expression of edr3 mRNA or protein in the presence of the candidate compound is compared to the level of expression of mRNA or protein in the absence of the candidate compound. The candidate compound can then be identified as a modulator of edr3 expression based on this comparison. For example, when expression of edr3 mRNA or protein is greater in the presence of the candidate compound than in its absence, the candidate compound is identified as a stimulator of edr3 mRNA or protein expression. Alternatively, when expression of edr3 mRNA or protein is less in the presence of the candidate compound than in its absence, the candidate compound is identified as an inhibitor of edr3 mRNA or protein expression. The level of edr3 mRNA or protein expression in the cells can be determined by methods described herein for detecting edr3 mRNA or protein.

Delivery of antisense, triplex agents, ribozymes, double stranded interfering RNA and the like can be achieved using a recombinant expression vector such as a chimeric virus or a colloidal dispersion system or by injection. Useful virus vectors include adenovirus, herpes virus, vaccinia, and/or RNA virus such as a retrovirus. The retrovirus can be a derivative of a murine or avian retrovirus such as Moloney murine leukemia virus or Rous sarcoma virus. All of these vectors can transfer or incorporate a gene for a selectable marker so that transduced cells can be identified and generated. The specific nucleotide sequences that can be inserted into the retroviral genome to allow target specific delivery of the retroviral vector containing an antisense oligonucleotide can be determined by one of skill in the art.

Another delivery system for polynucleotides is a colloidal dispersion system. Colloidal dispersion systems include macromolecular complexes, nanocapsules, microspheres, beads, and lipid-based systems including oil-in-water emulsions, micelles, mixed micelles and liposomes. A preferred colloidal delivery system is a liposome, an artificial membrane vesicle useful as in vivo or in vitro delivery vehicles. The composition of a liposome is usually a combination of phospholipids, usually in combination with steroids, particularly cholesterol.

Further, patients may be treated by gene replacement therapy. One or more copies of a normal target gene, or a portion of the gene that directs the production of a normal target gene protein with target gene function, may be inserted into cells using vectors that include, but are not limited to adenovirus, adenoma-associated virus, and retrovirus vectors, in addition to other particles that introduce DNA into cells, such as liposomes. Additionally, techniques such as those described above may be utilized for the introduction of normal target gene sequences into human cells.

The therapeutic composition can also be used to induce differentiation of a progenitor cell, e.g. in order to study the process of differentiation and test compounds which affect this process. Induction of differentiation is also desirable, for example, in the treatment of anaplastic tumors, which are composed of cells that have lost some of their differentiated characteristics. Progenitor cells which can be induced to differentiate using the therapeutic composition include, but are not limited to, erythropoietic stem cells, neuroblasts, chrondroblasts, melanoblasts, myoblasts, neural crest cells, and the like.

One embodiment herein accordingly comprises methods for the identification of small molecule drug candidates from large libraries of compounds that appear to have therapeutic activity to affect metabolic maintenance and/or to reverse or prevent cell death and thus exhibits potential therapeutic utility enhancing longevity. Small organic molecules and peptides having effective inhibitory activity may be designed de novo, identified through assays or screens, or obtained by a combination of the two techniques. Non-protein drug design may be carried out using computer graphic modeling to design non-peptide, organic molecules able to bind to the cellular transporters. The use of nuclear magnetic resonance (NMR) data for modeling is also known in the art, as described by Lam et al., *Science* 263: 380, 1994, using information from x-ray crystal structure studies of the transporter.

Small molecules may also be developed by generating a library of molecules, selecting for those molecules which act as ligands for a specified target, (using protein functional assays, for example), and identifying the selected ligands. See, e.g., Kohl et al., *Science* 260: 1934, 1993. Techniques for constructing and screening combinatorial libraries of small molecules or oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, 7 February 1994) and nonpeptide polymers (see, e.g., "peptoids" of Simon et al., *Proc. Natl. Acad. Sci. USA* 89 9367, 1992). See also U.S. Pat. No. 5,270,170 to Schatz; Scott and Smith, *Science* 249: 386-390, 1990; Devlin et al., *Science* 249: 404-406, 1990; Edgington, *BIO/Technology*, 11: 285, 1993. Libraries maybe synthesized in solution on solid supports, or expressed on the surface of bacteriophage viruses (phage display libraries).

Known screening methods may be used by those skilled in the art to screen combinatorial libraries to identify active molecules.

In one embodiment, assays for screening candidate or test compounds that are substrates of an EDR3 protein or polypeptide or biologically active portion thereof are provided. In another embodiment, assays for screening candidate or test compounds which bind to or modulate the activity of an EDR3 protein or polypeptide or biologically active portion thereof; e.g., modulate the ability of EDR3 to interact with a ligand.

Examples of methods for the synthesis of molecular libraries can be found in the art, for example in: DeWitt et al., *Proc. Natl. Acad. Sci. U.S.A.* 90: 6909, 1993; Erb. et al., *Proc. Natl. Acad. Sci. USA* 91: 11422, 1994; Zuckermann et al., *J. Med. Chem.* 37: 2678, 1994; Cho et al., *Science* 261: 1303, 1993; Carrell et al., *Angew. Chem. Int. Ed. Engl.* 33: 2059, 1994; Carell et al., *Angew. Chem. Int. Ed. Engl.* 33: 2061, 1994; and in Gallop et al., *J. Med. Chem.* 37:1233, 1994.

Libraries of compounds may be presented in solution (e.g., Houghten, *Biotechniques* 13: 412-421, 1992), or on beads (Lam, *Nature* 354: 82-84, 1991), chips (Fodor, *Nature* 364: 555-556, 1993), bacteria (Ladner U.S. Pat. No. 5,223, 409), spores (Ladner U.S. Pat. No. '409), plasmids (Cull et al., *Proc Natl Acad Sci USA* 89: 1865-1869, 1992) or on phage (Scott and Smith, *Science* 249: 386-390, 1990); (Devlin, *Science* 249: 404-406, 1990); (Cwirla et al., *Proc. Natl. Acad. Sci U.S.A.* 87: 6378-6382, 1990); (Felici, *J. Mol. Biol.* 222: 301-310, 1991); (Ladner supra.).

Candidate EDR3 interacting molecules encompass many chemical classes. They can be organic molecules, preferably small organic compounds having molecular weights of 50 to 2,500 daltons. The candidate molecules comprise functional groups necessary for structural interaction with proteins, particularly hydrogen bonding, for example, carbonyl, hydroxyl, and carboxyl groups. The candidate molecules can comprise cyclic carbon or heterocyclic structures and aromatic or polyaromatic structures substituted with the above groups.

Other techniques are known in the art for screening synthesized molecules to select those with the desired activity, and for labeling the members of the library so that selected active molecules may be identified, as in U.S. Pat. No. 5,283,173 to Fields et al., (use of genetically altered *Saccharomyces cerevisiae* to screen peptides for interactions). As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized fragments that are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology* 11: 285, 1993. U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA* 89: 8864, 1992; and Tsai and Keene, *J. Immunology* 150: 1137, 1993. In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

Also encompassed are assays for cellular proteins that interact with EDR3. A number of methods suitable for detecting protein-protein interactions are known. The traditional methods that may be used include, for example, co-immunoprecipitation, crosslinking, and co-purification through gradients or chromatographic columns. For these assays, EDR3 can be a full-length protein or an active fragment. Additional methods include those methods that allow for the simultaneous identification of genes that encode proteins that interact with EDR3. These methods include, for example, probing expression libraries using a labeled EDR3 protein, EDR3 fragment, or EDR3 fusion protein.

One method to detect protein-protein interaction in vivo is the two-hybrid system, see, for example, Chien et al., *Proc. Natl. Acad. Sci, USA* 88: 9578-9582, 1991. In brief, the two-hybrid system utilizes plasmids constructed to encode two hybrid proteins: one plasmid comprises the nucleotides encoding the DNA binding domain of a transcriptional activator protein fused to the edr3 nucleotide sequence encoding the EDR3 polypeptide, and the other plasmid comprises the nucleotides encoding the transcriptional activator protein's activation domain fused to a cDNA encoding an unknown protein that has been recombined into the plasmid from a cDNA library. The DNA binding domain fusion plasmid and the cDNA fusion protein library plasmids are transformed into a strain of yeast that contains a reporter gene, for example lacZ, whose regulatory region contains the activator's binding site. Either hybrid protein alone cannot activate translation of the reporter gene because it is lacking either the DNA binding domain or the activator domain. Interaction of the two hybrid proteins, however, reconstitutes a functional activator protein and results in activation of the reporter gene that is detected by an assay for the reporter gene product. The colonies that reconstitute activator activity are purified and the library plasmids responsible for reporter gene activity are isolated and sequenced. The DNA sequence is then used to identify the protein encoded by the library plasmid.

Macromolecules that interact with EDR3 are referred to as EDR3 binding partners. EDR3 binding partners are likely to be involved in the regulation of EDR3 function. Therefore, it is possible to identify compounds that interfere with the interaction between EDR3 and its binding partners. The basic principle of assay systems used to identify compounds that interfere with the interaction of EDR3 and a binding partner is to prepare a reaction mixture containing EDR3 or an EDR3 fragment and the binding partner under conditions that allow complex formation. The reaction mixture is prepared in the presence or absence of the test compound to test for inhibitory activity. The test compound may be added prior to or subsequent to EDR3/binding partner complex formation. The formation of a complex in a control but not with the test compound confirms that the test compound interferes with complex formation. The assay can be conducted either in the solid phase or in the liquid phase.

Another embodiment includes treatment of a mammal with a composition comprising all or a portion of an edr3 gene, particularly a wild-type edr3 gene or gene expression product in a pharmaceutically acceptable carrier. Such treatment is expected to be effective for alleviation of proliferative disorders, such as neoplasias, dysplasias, and hyperplasias, by administration of a therapeutic composition that enhances edr3 function to a cell, or that restores a wild-type edr3 function to a cell that has lost that function. Neoplasias which can be treated with the antisense composition include, but are not limited to, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, tumors of mixed origin, such as Wilms' tumor and teratocarcinomas, metastatic tumors, and the like. Proliferative disorders that can be treated with the therapeutic composition include disorders such as anhydric hereditary ectodermal dysplasia, congenital alveolar dysplasia, and epithelial dysplasia of the cervix, fibrous dysplasia of bone, mammary dysplasia, and the like. Hyperplasias, for example, endometrial, adrenal, breast, prostate, or thyroid hyperplasias or pseudoepitheliomatous hyperplasia of the skin can be treated with the edr3 restorative therapeutic compositions. Even in disorders in which edr3 mutations are not implicated, upregulation of edr3 expression can have therapeutic application. In these disorders, increasing edr3 expression can help to suppress tumors. Similarly, in tumors where edr3 expression is not aberrant, effecting edr3 upregulation can suppress metastases.

Pharmaceutically acceptable carriers include, but are not limited to, large, slowly metabolized macromolecules such as proteins, polysaccharides, polylactic acids, polyglycolic acids, polymeric amino acids, amino acid copolymers, inactive virus particles, and the like. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes, such as those described in U.S. Pat No. 5,422,120, WO 95/13796, WO 91/14445, or EP 524,968 B1, can also be used as a carrier for the therapeutic edr3 composition.

Typically, the sense or antisense edr3 composition is prepared as an injectable, either as a liquid solution or suspension. However solid forms suitable for solution in, or suspension in, liquid vehicles prior to injection can also be prepared. The composition can also be formulated into an enteric-coated tablet or gel capsule according to known methods in the art, such as those described in U.S. Pat No. 4,853,230, EP 225,189, AU 9,224,296, and AU 9,230,801.

Both the dose of the edr3 restorative composition (or the antisense composition) and the means of administration can be determined based on the specific qualities of the therapeutic composition, the condition, age, and weight of the patient, the progression of the disease, and other relevant factors. Administration of the therapeutic edr3 sense or antisense agents of the invention can include local or systemic administration, including injection, oral administration, particle gun, catheterized administration, topical administration, and the like. Preferably, the therapeutic sense or antisense composition contains an expression construct comprising a promoter and a polynucleotide segment of 12 to 3000 contiguous nucleotides of the sense or antisense strand of edr3. Within the expression construct, the polynucleotide segment is located downstream from the promoter, and transcription of the polynucleotide segment initiates at the promoter. Various methods can be used to administer the therapeutic composition directly to a specific site in the body. For example, a small metastatic lesion can be located and the therapeutic composition injected several times in several different locations within the body of tumor. Alternatively, arteries that serve a tumor can be identified, and the therapeutic composition injected into such an artery, in order to deliver the composition directly into the tumor. A tumor that has a necrotic center can be aspirated and the composition injected directly into the now empty center of the tumor. The sense or antisense edr3 composition can be directly administered to the surface of the tumor, for example, by topical application of the composition. X-ray imaging can be used to assist in certain of the above delivery methods.

Receptor-mediated targeted delivery of therapeutic compositions containing edr3 subgenomic sense or antisense polynucleotides to specific tissues can also be used. Receptor-mediated DNA delivery techniques are described in, for example, Findeis et al. (1993), Trends in Biotechnol. 11, 202-05; Chiou et al. (1994), GENE THERAPEUTICS: METHODS AND APPLICATIONS OF DIRECT GENE TRANSFER (J. A. Wolff, ed.); Wu & Wu (1988), J. Biol. Chem. 263, 621-24; Wu et al. (1994), J. Biol. Chem. 269, 542-46; Zenke et al. (1990), Proc. Natl. Acad. Sci. U.S.A. 87, 3655-59; Wu et al. (1991), J. Biol. Chem. 266, 338-42.

Alternatively, the composition containing subgenomic sense or antisense edr3 polynucleotides can be introduced into human cells ex vivo and then replaced into the human. Cells can be removed from a variety of locations including, for example, from a selected tumor or from an affected organ. In addition, the therapeutic sense or antisense composition can be inserted into non-tumorigenic cells, for example, dermal fibroblasts or peripheral blood leukocytes. If desired, particular fractions of cells such as a T cell subset or stem cells can also be specifically removed from the blood (see, for example, PCT WO 91/16116). The edr3 therapeutic composition can then be contacted with the removed cells utilizing any of the above-described techniques, followed by the return of the cells to the human, preferably to or within the vicinity of a tumor. The above-described methods can additionally comprise the steps of depleting fibroblasts or other non-contaminating tumor cells subsequent to removing tumor cells from a human, and/or the step of inactivating the cells, for example, by irradiation.

More complete descriptions of gene therapy vectors, especially retroviral vectors are contained in U.S. Pat. Nos. 6,190,907; 6,140,111; 6,096,534; 5,741,486; and 5,714,353 and in EP0827545 which are incorporated herein by reference.

Therapeutic compositions containing edr3 subgenomic polynucleotides can be administered at about 80 nanograms (ng) to about 240 milligrams (mg) of DNA for local administration in a gene therapy protocol. Within this range, greater than about 90 ng is preferred, with greater than about 100 ng more preferred. Within this range, less than about 220 mg is preferred, with less than about 200 mg more preferred. Concentration ranges of about 0.5 mg to about 50 mg, about 1 microgram to about 2 mg, about 5 microgram to about 500 microgram, and about 20 microgram to about 100 microgram of DNA can also be used during a gene therapy protocol. Factors such as method of action and efficacy of transformation and expression are considerations that will effect the dosage required for ultimate efficacy of the edr3 subgenomic sense or antisense polynucleotides. Where greater expression is desired over a larger area of tissue, larger amounts of edr3 subgenomic sense or antisense polynucleotides or the same amounts readministered in a successive protocol of administrations, or several administrations to different adjacent or close tissue portions of for example, a tumor site, may be required to effect a positive therapeutic outcome. In all cases, routine experimentation in clinical trials will determine specific ranges for optimal therapeutic effect.

The invention is further illustrated by the following non-limiting examples.

EXAMPLES

Example 1

Isolation of a Candidate Gene from Within the Critical Region for Both Osteosarcoma and CDLS Sequence information for the initial edr3 clone was obtained from two human ESTs: E5T1367617 and EST1352182 (GenBank AA810014 and AA808201 respectively). These two clones are part of the Unigene cluster Hs.123311. Both clones were obtained (Research Genetics) and sequenced and the consensus sequence used to design primers for PCR. The 5' end of edr3 was obtained by screening a human skeletal muscle StretchPlus™ cDNA library (Clontech Laboratories). PvuII restriction fragments from the 5' end of EST1367617 were used as the probe for the primary screening. SacI restriction fragment upstream of the 5' end of EST1367617 was used as a probe for subsequent screenings. The probes were labeled using Rediprime®, DNA labeling random priming system (Amersham-Pharmacia). Positive clones were amplified in liquid culture and phage DNA was purified using Lambda purification kit (Life Technologies) and sequenced. The clones with the largest insert were chosen to be sequenced.

Using the two ESTs, a full-length cDNA clone containing these ESTs encoding a novel member of the polycomb gene superfamily was isolated and named edr3. The complete mRNA sequence was submitted to GenBank (Accession No. AF380154). The human edr3 gene is SEQ ID NO:1 and the human EDR polypeptide is SEQ ID NO:2. The cDNA was 3319 base pairs and contained an open reading frame of 2895 base pairs which in turn encoded a protein sequence of 964 amino acids.

Example 2

Isolation of a Human Genomic cDNA edr3 Clone

A human genomic clone was isolated by screening a human genomic phage library (Stratagene). For reverse transcription PCR, total RNA from normal human mesenchymal stem cells (hMSC) and human placenta was isolated using ToTALLYRNA™ total RNA isolation kit (Ambion). The reverse transcription reaction primed with gene specific primer EDR3(1589)R5'-GCTGCACTTGTAAAGACTG-CATAG-3' (SEQ ID NO:5) was carried out using SuperScript™II reverse transcriptase (Life Technologies) for 75 minutes at 42° C. PCR amplification was performed using EDR3(1289)R primer, 5'-ATGACACAAGAGGGT-GTGGC-3' (SEQ ID NO:6) and EDR3(84)F primer 5'-CGG-GAACATCTTCTGTGTCAAC-3' (SEQ ID NO:7). GAPDH was used as an internal control. Resulting PCR fragment was gel purified using CONCERT™ rapid gel extraction system (Life Technologies) and cloned into pCR®II TOPO®-TA cloning vector (Invitrogen). Cloned plasmid was transformed into TOP 10 competent cells. Plasmid DNA was extracted by alkaline lysis and sequenced.

Figure 2:
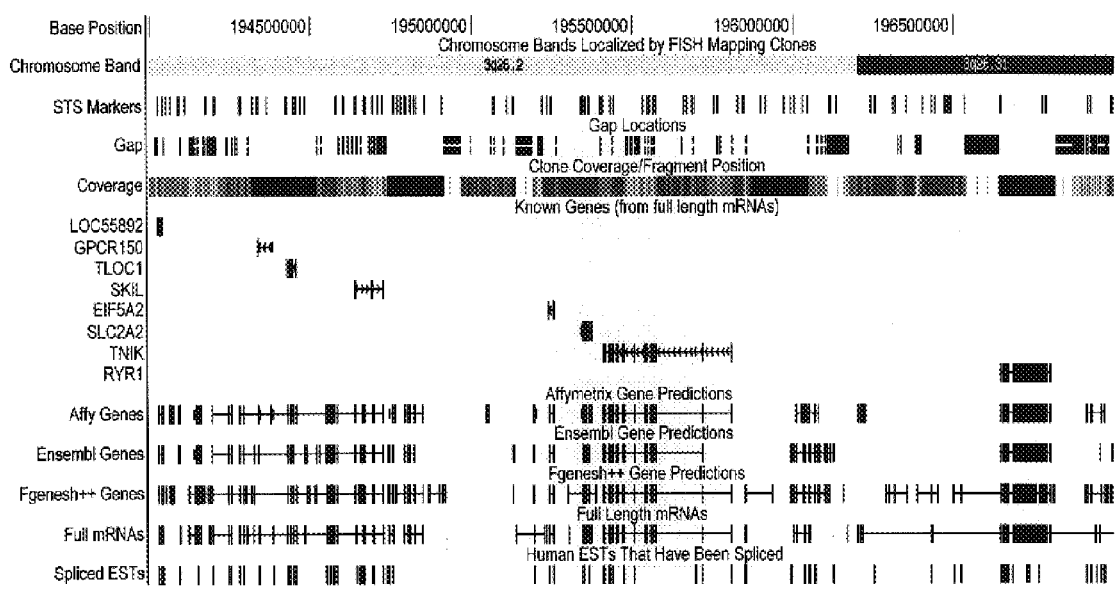
FIG. 2 is a schematic of a broader map of the region including edr3.

Additional information on the genomic structure of the edr3 gene was obtained from the GenBank database. BAC sequence information was obtained from the Genbank database and the BAC contig assembly was analyzed using the BAC contig data from the San Antonio Genome Center and the Genome Center at the University of Santa Clara. MacVector™ comprehensive sequence analysis software (Oxford Molecular) was used for sequence assembly and analysis, either alone or with BLAST ((Basic Local Alignment Search Tool, NCBI), Autoassembler, GRAIL, Genefinder and EditView (PB Biosystems). Analysis tools available on the Expasy website were used to analyze the translation and protein sequence for identification of conserved or functional domains. The genomic region surrounding the edr3 gene on human chromosome 3 is shown in FIG. 1. A broader map of the region including edr3 is shown in FIG. 2.

Example 3

Isolation of the Mouse edr3 and Comparison of Protein Sequences

The mouse ortholog of edr3 was also cloned and sequenced by techniques known in the art. The mouse edr3 gene is SEQ ID NO:3. FIG. 3 shows the homology between human EDR3, mouse EDR3 and two members of the polycomb family, EDR1 and EDR2. The proteins share significant sequence identity with EDR3 and EDR1 (SEQ ID NO:8) at 56% identity, EDR3 and EDR2 (SEQ ID NO: 9) at 48% identity and human and mouse EDR3 at 98% homology.

Example 4

Expression of Human edr3 in Human Tissues

Figure 4:
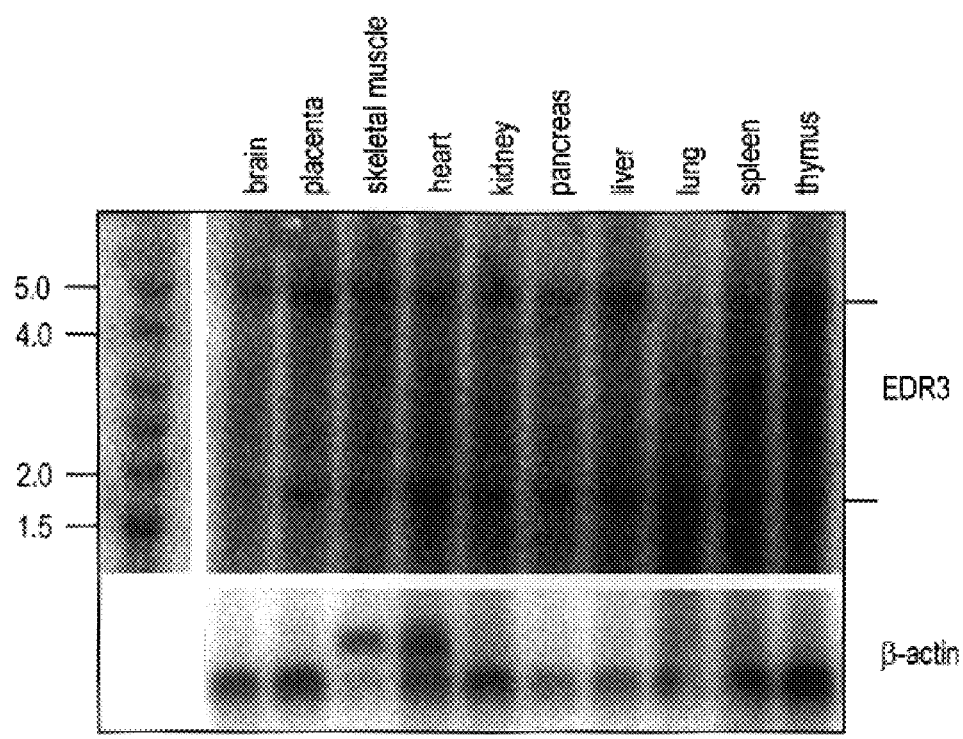
FIG. 4 shows Northern analysis of edr3. Northern analysis of multiple-tissue blots using the edr3 cDNA as a probe demonstrates two signals corresponding to a 4.8 kb mRNA and a smaller 2.0 kb mRNA that may be an alternative splice form. Beta-actin was hybridized to the same blot as a control.

Northern analysis was performed on prepared blots (Ambion FirstChoice™, prepared Northern blots) using the edr3 cDNA as a probe following the manufacturer's recommendation. Northern analysis of multiple tissue blots using the edr3 cDNA as a probe demonstrates two signals corresponding to a 4.8 kb mRNA and a smaller 2.0 kb RNA that may be an alternate splice form (FIG. 4). Beta-actin was used on the same blot as a control.

Example 5

Edr3 Expression in Developing Mouse Embryos

In situ hybridization on human fetal limbs, mouse embryos and tissue culture cells were performed as described in Ausubel, Fm et el, Ed. (In Situ Hybridization and Immunochemistry, John Wiley & Sons, 1993) with the following modifications. The least conserved regions of edr3 were cloned into pT7T3D cloning vector, to generate riboprobes. The riboprobes were directly labeled with Alexafluor®-488 UTP (Molecular Probes) and purified using Sephadex-G50 columns (Roche). Slides were viewed on an Olympus BX-60 microscope and images were captured using the OpenLAB™ software by Improvision.

Figure 5:
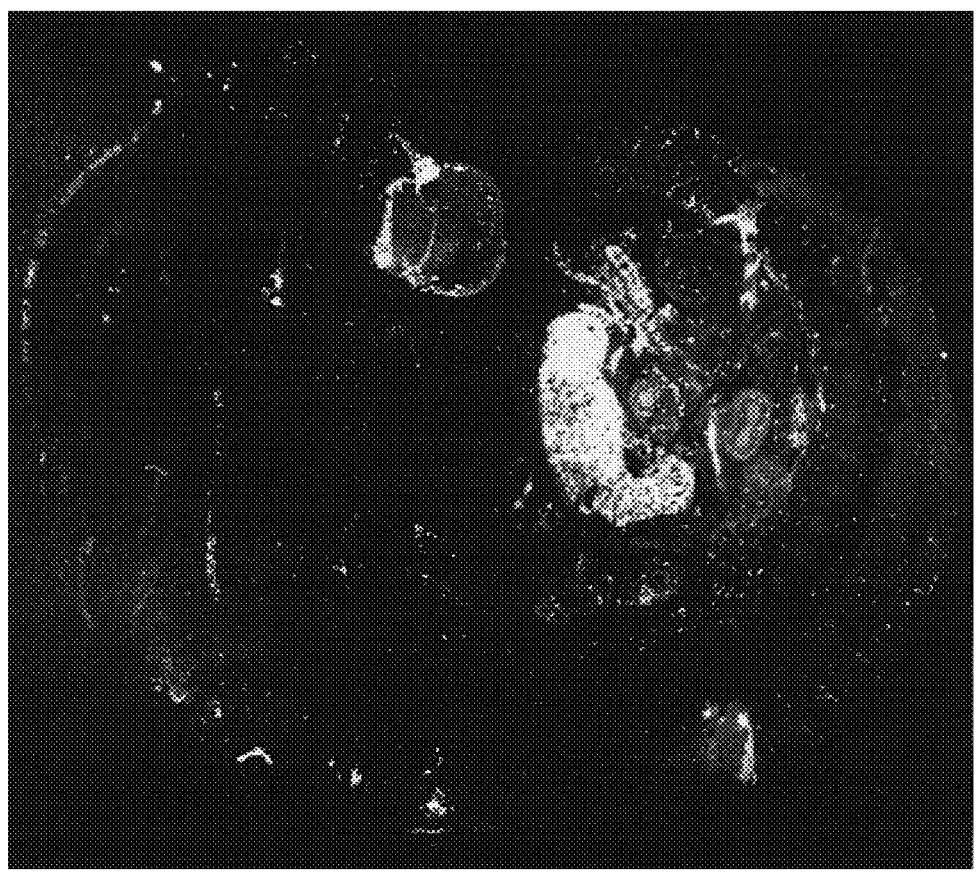
FIG. 5 shows edr3 expression in a 12.5 dpc mouse embryos by in situ hybridization. Alexafluor®-488-labeled mouse probe was used for all the in situ experiments shown in this figure. Expression is seen in the roof of the neopallial cortex (which will form the cerebral cortex) (cc) as well as the lung and the condensing mesenchymal layers in the cartilage primordium in the vertebral bodies (vb)

Using the mouse edr3 cDNA, we examined mouse embryos from 12.5 days post-conception (dpc), 13.5 dpc and 14.5 dpc by in situ hybridization. This timeframe was chosen to include the stages in which the overall shape of the embryo begins to change and take on the adult-like features. Also within this timeframe, the limb precartilage models are replaced by cartilage and the morphology of the feet changes; the digital interzones retreat and the digits emerge as separate units. FIG. 5 shows that at 12.5 dpc, expression of edr3 is seen in the roof of the midbrain, the lung and the cartilage primordium of the vertebral bodies, the nasopharyngeal region, liver and stomach.

Figure 6:
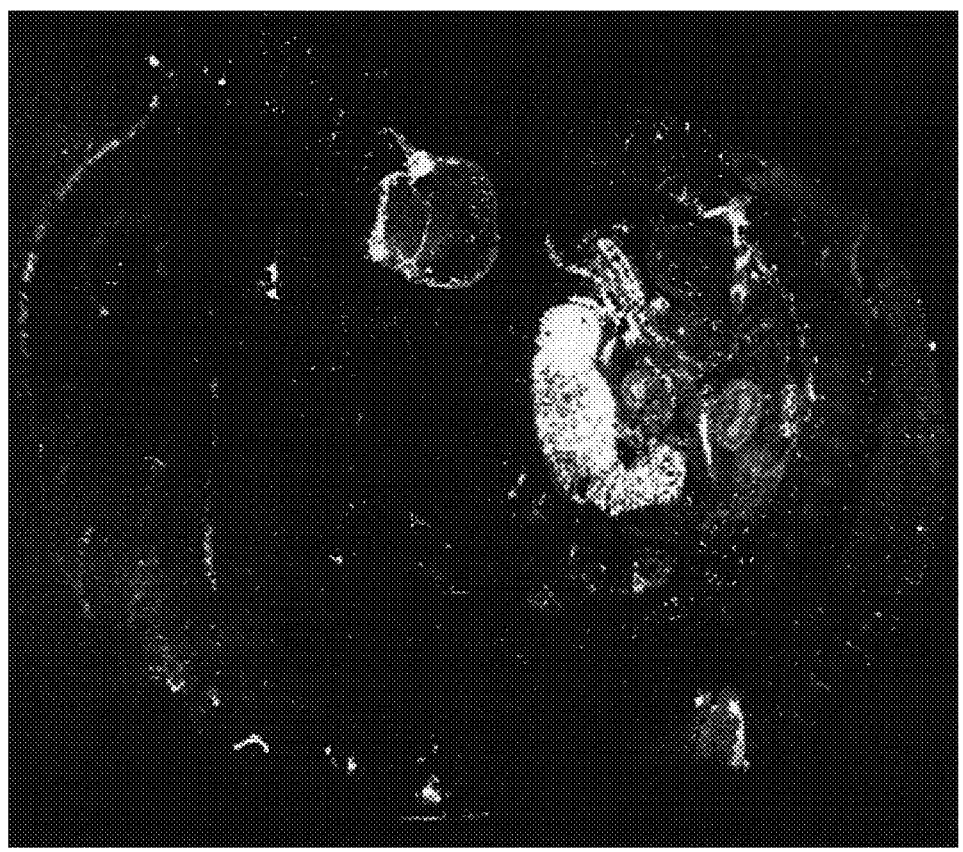
FIG. 6 shows edr3 expression in a 13.5 dpc mouse embryo by in situ hybridization. Edr3 expression is seen in the diencephalon (dc), the Rathke's pouch (the pituitary) (rp), the choroid plexus (cp), the upper lip (lip) and the base of a tooth bud (tb)

FIG. 6 shows that at 13.5 dpc, expression of edr3 is seen throughout the brain, the roof of the neopallial cortex (which will develop into the cerebral cortex), and Rathke's pouch (the developing pituitary), as well as the nasopharyngeal region including the base of the primordial tooth and upper and lower lips. Expression can also be seen in the choroid plexus and the liver and heart.

Figure 7:
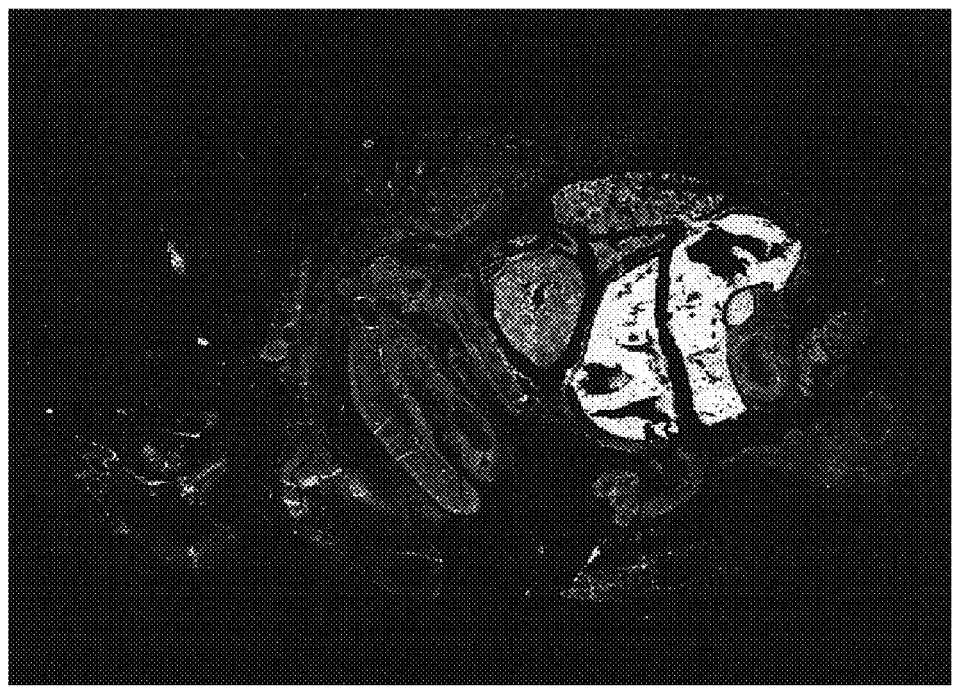
FIG. 7 shows edr3 expression in a 14.5 dpc mouse embryo by in situ hybridization. Edr3 expression is seen in the roof of the neopallial cortex (cc), the choroid plexus, the mesenchymal layers surrounding the vertebrae (vb) and other bones including the developing femur (f). Edr3 is also expressed in the tongue (t) and the mandible (mn) as well as in the lung.
Figure 8A:
FIG. 8 shows Fluorescent in situ hybridization of an EDR3 containing BAC genomic clone to lymphoblastoid cells derived from CDLS patients. BAC RPC11-379k17 which contains the 3' portion of the EDR3 gene was used as a probe to metaphase spreads of cells from patients with CDLS. a, Patient CDLS-1 had a 3:22 translocation which carried an additional copy of the EDR3 (arrow). Green dots show hybridization to the chromosome 3q26.3-containing regions. The arrow indicated the translocation chromosome 3q26.3-q26.3 region.
Figure 8B:
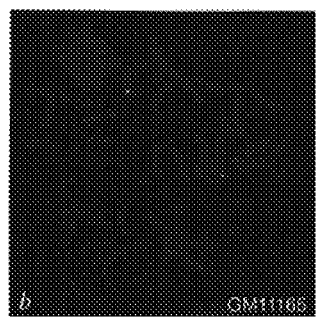
Figure 8C:
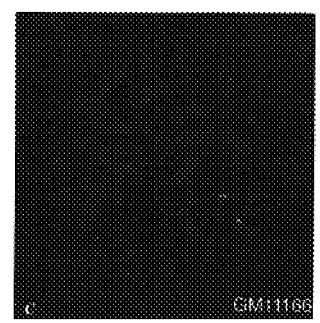
Figure 8D:
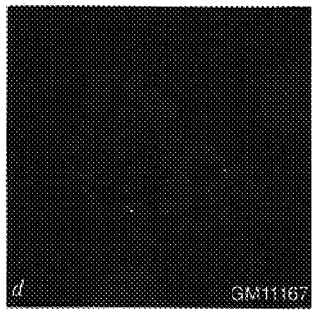
Figure 8E:
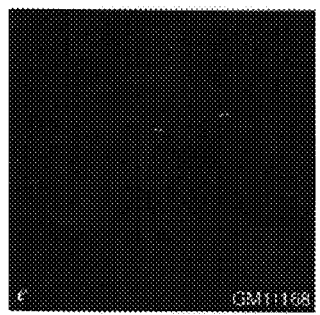

By 14.5 dpc, expression of edr3 is seen to focus in the roof of the neopallial cortex, the tongue and the condensing mesenchyme of the nose, lower jaw, vertebrae and femur. Edr3 is expressed strongly in the heart, liver and lung (FIG. 7). Of particular interest is the expression of edr3 in the developing digits of the limb, suggesting that edr3 is involved in these peripheral limb structures as well. Thus, the expression of edr3 during this crucial stage of embryogenesis involves the brain, choroid plexus, heart, liver and lungs. It is also expressed in the skull, the nasopharyngeal region including the jaws, lips, and nose and the models of the developing limbs (including the digits) and other bones.

Example 6

Duplication of the edr3 Gene in Cell Lines Derived from Patients with CdLS

The expression pattern of edr3 seen in the mouse suggested that the human edr3 might be a candidate gene for CDLS/dup(3q) syndrome as many of tissues in which edr3 was expressed are frequently affected in patients with dup (3q) syndrome or CDLS. Both syndromes have characteristic craniofacial features including microbrachycephaly and micrognathia, as well as cardiac, genitourinary and lung abnormalities. A key difference between the two syndromes is the limb abnormalities seen in CDLS patients but not in dup(3q) syndrome patients. Thus, expression of edr3 in the limbs and developing cartilage models of bone suggested that edr3 may more critical in CDLS than in the dup(3q) syndrome.

To test whether edr3 is duplicated in CDLS patients, as would be expected of a critical CDLS gene candidate, we examined lymphoblastoid cell lines derived from CDLS patients (Table 1) for duplications of the edr3 gene.

TABLE 1

Summary of information regarding karyotype and clinical features of CDLS patients from which the lymphoblastoid cell lines used in this study were derived.

| Cell Line | Karyotype | Description of Clinical Phenotype |
|---|---|---|
| GM11165 | 46, XY | 8 years old, low birth weight, borderline head circumference; hirsute; low post hairline; confluent eyebrows; long lashes; broad nasal bridge; palate; micrognathia; clinodactyly of 5th fingers; web toes |
| GM11166 | 46, XY | 2 years old, slightly small head circumferance; no hirsutism; low post hairline; confluent eyebrows; long lashes; broad nasal bridge; anteverted prominent philtrum; high arched nostrils; prominent philtrum; high arched palate; low cry; small hands and feet; clinodactyly of 5th fingers |
| GM11167 | 46, XX | 23 years old, low birth weight; small head circumference; hirsutism; low hairline; confluent eyebrows; long lashes; broad nasal bridge; anteverted nostrils; prominent philtrum; low pitched cry; small hands and feet; clinodactyly of 5th fingers; cutis marmorata |
| GM11168 | 46, XY | 5 years old, small head circumference; low birth weight; mild hirsutism; low post hairline; mass confluence of eyebrows; broad nasal bridge; anteverted nostrils; prominent philtrum; cleft palate; micrognathia; small hands and feet; webbed toes; hearing difficulty |
| GM10266 | 46, XY, −22, +der(22)t(3; 22) (22qter > 22p12::3q25.3 > 3qter) | 38 years old, developmental delay, profound retardation; seizures; microbrachycephaly; synophrys, prominent philtrum, high arched palate, micrognathia, low set ears, clinodactyly of 5th fingers; 3 cousins are also affected |
| WI-38 | 46, XX | normal control fibroblasts |

Cell lines were tested using a fluorescent in situ hybridization (FISH) assay. Metaphase chromosome spreads were isolated from lymphoblastoid cell lines using colcemid and ethidium bromide using the methods of Ikeuchi (Ikeuchi, T., Cytogenet. Cell. Genet. 38, 56-61 (1984)). The FISH analyses were performed as previously described (Keppler-Noreuil, K M, et al., Am J Med Genet. 76: 372-378 (1998)). Briefly, the chromosomes were hybridized with fluorescein isothiocyanate (FITC)-labeled DNA from BAC RPCI11-379k17 (AC008040) containing the EDR3 gene was used as a probe. Chromosomes were counterstained with DAPI II (Vysis). Similar results were obtained with BAC clones RPCI11-362k14 (AC078795) and RPCI13-81O8 (AC023891) (results not shown). Together, these BAC clones spanned the EDR3 genomic sequence.

In one cell line derived from a patient with CDLS in which a 3:22 translocation resulted in a partial trisomy of chromosome 3q, FISH analysis revealed that the region containing the genomic edr3 sequence was present in three copies (FIG. 8). In four other cell lines from karyotypically normal CDLS patients, FISH analysis showed only two apparent copies of the edr3 region (FIG. 10a-e) suggesting that any tandem duplication event that might have occurred might be below the resolution of FISH analysis. To test this, we examined the cell lines by both FISH analysis using dual colored probes. Dual color FISH analysis showed two signals in all four karyotypically normal samples (data not shown).

Example 7

Quantitative Southern Hybridization of DNA from CdLS Patients

Quantitative hybridization was performed as described in Hansen, MF (Proc. Nati. Acad. Sci. U.S.A. 82, 6216-20 (1985)). Briefly, DNAs from the CDLS patients and normal controls were digested with EcoRI and PstI and fragments separated by agarose gel electrophoresis and transferred to nylon membranes and hybridized to radioactively-labeled probes prepared using the Rediprime® DNA labeling random priming system (Amersham-Pharmacia). The number of copies of each gene present per cell was determined by comparing the hybridization signals of edr3 and SHOX2 to those of an unrelated chromosome 13 probe, pHU10 (D13S6) as a diploid control. The probes were hybridized concurrently and the hybridization signals measured using a phosphor-imager (Molecular Dynamics). The hybridization signals for edr3 and SHOX2 were normalized to the pHU10 signal. Each analysis was performed three times and the results averaged. The normalized values were then used to determine copy number/cell.

Southern analysis on the cell line DNA revealed that edr3 is present in increased copy number consistent with a duplication of edr3 (FIG. 9, Table 2). In contrast, SHOX2, a gene which had previously been suggested as a candidate for the CDLS locus, was found in increased copy number in only one cell line (FIG. 9, Table 2) suggesting that the duplication event involving edr3 was generally small.

TABLE 2

Quantitative Southern hybridization analysis of edr3 and SHOX2 in karyotypically normal patient DNAs.

| Cell line | Average Number of Copies of EDR3/Cell | Average Number of Copies of SHOX2/Cell |
|---|---|---|
| WI-38 (control) | 2.0 | 2.0 |
| GM11165 | 3.4 | 3.0 |
| GM11166 | 2.7 | 2.0 |
| GM11167 | 2.7 | 1.5 |
| GM11168 | 3.0 | 1.5 |

The present disclosure is directed to the discovery of the polynucleotide encoding EDR3, a novel early development regulator. Edr3 is implicated in CdLs, a genetic disorder, and in neoplastic disease. The edr3 polynucleotides and polypeptides have many uses including genetic testing for CdLs and somatic gene therapy for neoplastic disease such as osteosarcoma. The edr3 gene can be used to diagnose neoplastic disease and to detect genetic predisposition to neoplasia in a human or animal. The edr3 gene and polypeptides are also useful for studying development.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An isolated polynucleotide selected from the group consisting of SEQ ID NO:1, SEQ ID NO:1 wherein T can also be U, the nucleic acid sequence complementary to SEQ ID NO:1, and the nucleic acid sequence fully complementary to SEQ ID NO:1 wherein T can also be U.

2. An expression vector comprising a polynucleotide according to claim 1.

3. The expression vector of claim 2 wherein the expression vector is selected from the group consisting of a bacterial, a yeast, an insect, and a mammalian expression vector.

4. The expression vector of claim 2 further comprising nucleotides encoding a second protein segment.

5. An isolated host cell comprising the expression vector of claim 2.

6. An isolated polynucleotide encoding the amino acid sequence as set forth in SEQ ID NO:2.

* * * * *

SEQUENCE LISTING

```
<160> NUMBER OF SEQ ID NOS: 4

<210> SEQ ID NO 1
<211> LENGTH: 3319
<212> TYPE: DNA
<213> ORGANISM: Homo sapiens

<400> SEQUENCE: 1
tggaggagag aagatggcgg aagcggagtg agtgactaga tgatttaagg accatagtac      60
agctatggat actgaaccaa acccgggaac atcttctgtg tcaacaacaa ccagcagtac     120
caccaccacc accatcacca cttcctcctc tcgaatgcag cagccacaga tctctgtcta     180
cagtggttca gaccgacatg ctgtacaggt atttcaacag gcattgcatc ggccccccag     240
ctcagctgct cagtaccttc agcaaatgta tgcagcccaa caacagcact tgatgctgca     300
tactgcagct cttcagcagc agcatttaag cagctcccag cttcagagcc ttgctgctgt     360
tcaggcaagt ttgtccagtg gaagaccatc tacatctccc acaggaagtg tcacacagca     420
gtcaagtatg tcccaggctt ccagttctac cagcggcagt attacccaac agactatgtt     480
actagggagt acttccccta ccctaacggc aagccaagct caaatgtatc tccgagctca     540
aatgctgatt ttcacacccg ctaccactgt ggctgctgta cagtctgaca ttcctgttgt     600
ctcgtcgtca tcgtcatctt cctgtcagtc tgcagctact caggttcaga atttaacatt     660
acgcagccag aagttgggtg tattatctag ctcacagaat ggtccaccaa aaagcactag     720
tcaaactcag tcattgacaa tttgtcataa caaaacaaca gtgaccagtt ctaaaatcag     780
ccaacgagat ccttctccag aaagtaataa gaaaggagag agcccaagcc tggaatcacg     840
aagcacagct gtcacccgga catcaagtat tcaccagtta atagcaccag cttcatattc     900
tccaattcag cctcattctc taataaaaca tcagcagatt cctcttcatt caccaccttc     960
caaagtttcc catcatcagc tgatattaca acagcagcaa cagcaaattc agccaatcac    1020
acttcagaat tcaactcaag acccaccccc atcccagcac tgtataccac tccagaacca    1080
tggccttcct ccagctccca gtaatgccca gtcacagcat tgttcaccga ttcagagtca    1140
tccctctcct ttaacagtgt ctcctaatca gtcacagtca gcacagcagt ctgtagtggt    1200
gtctcctcca ccacctcatt caccaagtca gtctcctact ataattattc atccacaagc    1260
acttattcag ccacacccctc ttgtgtcatc agctctccag ccagggccaa atttgcagca    1320
gtccactgct aatcaggtgc aagctacagc acagttgaat cttccatccc atcttccact    1380
tccagcttcc cctgttgtac acattggccc agttcagcag tctgccttgg tatcccagg    1440 ccagcagatt gtctctccat cacaccagca atattcatcc ctgcagtcct ctccaatccc    1500
aattgcaagt cctccacaga tgtcgacatc tcctccagct cagattccac cactgcccctt    1560 gcagtctatg cagtctttac aagtgcagcc tgaaattctg tccagggcc aggttttggt    1620 gcagaatgct ttggtgtcag aagaggaact tccagctgca gaagctttgg tccagttgcc    1680
```

-continued

```
atttcagact cttcctcctc cacagactgt tgcggtaaac ctacaagtgc aaccaccagc    1740
acctgttgat ccaccagtgg tttatcaggt agaagatgtg tgtgaagaag aaatgccaga    1800
agagtcagat gaatgtgtcc ggatggatag aaccccacca ccacccactt tgtctccagc    1860
agctataaca gtggggagag gagaagattt gacttctgaa catcctttgt tagagcaagt    1920
ggaattacct gctgtggcat cagtcagtgc ttcagtaatt aaatctccat cagatccctc    1980
acatgtttct gttccaccac ctccattgtt acttccagct gccaccacaa ggagtaacag    2040
tacatctatg cacagtagca ttcccagtat agagaacaaa cctccacagg ctattgttaa    2100
accacagatc ctaacccatg ttattgaagg ctttgtgatt caggagggat tggagccatt    2160
tcctgtgagt cgttcctctt tgctaataga acagcctgtg aaaaaacggc tctcttttgga   2220 taatcaggtg ataaattcag tgtgtgttca gccagagcta cagaataata caaaacatgc    2280
ggataattca tctgacacag atgggaaga catgattgct gaagagacat tagaagaaat     2340
ggacagtgag ttgctcaagt gtgaattctg tgggaaaatg ggatatgcta atgaattttt    2400
gcggtcaaaa cgattctgca ctatgtcatg tgccaaaagg tacaatgtta gctgttctaa    2460
aaaatttgca cttagtcgtt ggaatcgtaa gcctgataat caaagtcttg ggcatcgtgg    2520
ccgtcgtcca agtggccctg atggggcagc gagagaacat atccttaggc agcttccaat    2580
tacttatcca tctgcagaag aagacttggc ttctcatgaa gattctgtgc catctgctat    2640
gacaactcgt ctgcgcaggc agagcgagcg ggaaagagaa cgtgagcttc gggatgtgag    2700
aattcggaaa atgcctgaga acagtgactt gctaccagtt gcacaaacag agccatctat    2760
atggacagtt gatgatgtct gggccttcat ccattctttg cctggttgcc aggatatcgc    2820
agatgaattc agagcacagg agattgatgg acaggccctt ctcttgctga agaagacca    2880 tctcatgagt gcaatgaata tcaagctagg cccagccctg aagatctgtg cacgcatcaa    2940
ctctctgaag gaatcttaac aggaacatga agccttgata aaacagcagt tttacttttc    3000
tcacaaaaac ttgtaaggta aaggcctaac ttggtctaga atatgacact tattgtggtg    3060
gatagccaag cacattggga tctccacatc aaatactgac atttcttcta caggtataat    3120
aattcatcat gcatttcat aattaataaa cattggtaaa attaatttta caggttacat     3180
gaaacattga aagacttgtt acagagggcc atgatatttt tcaaagaaat gtgttatact    3240 agataattt tttaaaggtg atgtttatca ttaatataaa gaatcctttt aaaagtaatt     3300
taatgattta catttctcc                                                 3319
```

<210> SEQ ID NO 2
<211> LENGTH: 964
<212> TYPE: PRT
<213> ORGANISM: Homo sapiens

<400> SEQUENCE: 2

```
Met Asp Thr Glu Pro Asn Pro Gly Thr Ser Val Ser Thr Thr Thr
1               5                   10                  15

Ser Ser Thr Thr Thr Thr Thr Ile Thr Thr Ser Ser Arg Met Gln
                20                  25                  30

Gln Pro Gln Ile Ser Val Tyr Ser Gly Ser Asp Arg His Ala Val Gln
            35                  40                  45

Val Phe Gln Gln Ala Leu His Arg Pro Pro Ser Ser Ala Ala Gln Tyr
        50                  55                  60

Leu Gln Gln Met Tyr Ala Ala Gln Gln Gln His Leu Met Leu His Thr
65                  70                  75                  80
```

-continued

```
Ala Ala Leu Gln Gln Gln His Leu Ser Ser Gln Leu Gln Ser Leu
                85                  90                  95

Ala Ala Val Gln Ala Ser Leu Ser Ser Gly Arg Pro Ser Thr Ser Pro
            100                 105                 110

Thr Gly Ser Val Thr Gln Gln Ser Ser Met Ser Gln Ala Ser Ser Ser
        115                 120                 125

Thr Ser Gly Ser Ile Thr Gln Gln Thr Met Leu Leu Gly Ser Thr Ser
    130                 135                 140

Pro Thr Leu Thr Ala Ser Gln Ala Gln Met Tyr Leu Arg Ala Gln Met
145                 150                 155                 160

Leu Ile Phe Thr Pro Ala Thr Val Ala Ala Val Gln Ser Asp Ile
                165                 170                 175

Pro Val Val Ser Ser Ser Ser Ser Cys Gln Ser Ala Ala Thr
                180                 185                 190

Gln Val Gln Asn Leu Thr Leu Arg Ser Gln Lys Leu Gly Val Leu Ser
            195                 200                 205

Ser Ser Gln Asn Gly Pro Pro Lys Ser Thr Ser Gln Thr Gln Ser Leu
210                 215                 220

Thr Ile Cys His Asn Lys Thr Thr Val Thr Ser Ser Lys Ile Ser Gln
225                 230                 235                 240

Arg Asp Pro Ser Pro Glu Ser Asn Lys Lys Gly Glu Ser Pro Ser Leu
                245                 250                 255

Glu Ser Arg Ser Thr Ala Val Thr Arg Thr Ser Ser Ile His Gln Leu
            260                 265                 270

Ile Ala Pro Ala Ser Tyr Ser Pro Ile Gln Pro His Ser Leu Ile Lys
        275                 280                 285

His Gln Gln Ile Pro Leu His Ser Pro Pro Ser Lys Val Ser His His
    290                 295                 300

Gln Leu Ile Leu Gln Gln Gln Gln Gln Ile Gln Pro Ile Thr Leu
305                 310                 315                 320

Gln Asn Ser Thr Gln Asp Pro Pro Ser Gln His Cys Ile Pro Leu
                325                 330                 335

Gln Asn His Gly Leu Pro Pro Ala Pro Ser Asn Ala Gln Ser Gln His
            340                 345                 350

Cys Ser Pro Ile Gln Ser His Pro Ser Pro Leu Thr Val Ser Pro Asn
        355                 360                 365

Gln Ser Gln Ser Ala Gln Gln Ser Val Val Ser Pro Pro Pro
    370                 375                 380

His Ser Pro Ser Gln Ser Pro Thr Ile Ile Ile His Pro Gln Ala Leu
385                 390                 395                 400

Ile Gln Pro His Pro Leu Val Ser Ser Ala Leu Gln Pro Gly Pro Asn
                405                 410                 415

Leu Gln Gln Ser Thr Ala Asn Gln Val Gln Ala Thr Ala Gln Leu Asn
            420                 425                 430

Leu Pro Ser His Leu Pro Leu Pro Ala Ser Pro Val Val His Ile Gly
        435                 440                 445

Pro Val Gln Gln Ser Ala Leu Val Ser Pro Gly Gln Gln Ile Val Ser
    450                 455                 460

Pro Ser His Gln Gln Tyr Ser Ser Leu Gln Ser Pro Ile Pro Ile
465                 470                 475                 480

Ala Ser Pro Pro Gln Met Ser Thr Ser Pro Pro Ala Gln Ile Pro Pro
                485                 490                 495
```

```
Leu Pro Leu Gln Ser Met Gln Ser Leu Gln Val Gln Pro Glu Ile Leu
            500                 505                 510

Ser Gln Gly Gln Val Leu Val Gln Asn Ala Leu Val Ser Glu Glu Glu
        515                 520                 525

Leu Pro Ala Ala Glu Ala Leu Val Gln Leu Pro Phe Gln Thr Leu Pro
    530                 535                 540

Pro Pro Gln Thr Val Ala Val Asn Leu Gln Val Gln Pro Pro Ala Pro
545                 550                 555                 560

Val Asp Pro Pro Val Val Tyr Gln Val Glu Asp Val Cys Glu Glu Glu
                565                 570                 575

Met Pro Glu Glu Ser Asp Glu Cys Val Arg Met Asp Arg Thr Pro Pro
            580                 585                 590

Pro Pro Thr Leu Ser Pro Ala Ala Ile Thr Val Gly Arg Gly Glu Asp
        595                 600                 605

Leu Thr Ser Glu His Pro Leu Leu Glu Gln Val Glu Leu Pro Ala Val
    610                 615                 620

Ala Ser Val Ser Ala Ser Val Ile Lys Ser Pro Ser Asp Pro Ser His
625                 630                 635                 640

Val Ser Val Pro Pro Pro Leu Leu Leu Pro Ala Ala Thr Thr Arg
                645                 650                 655

Ser Asn Ser Thr Ser Met His Ser Ser Ile Pro Ser Ile Glu Asn Lys
            660                 665                 670

Pro Pro Gln Ala Ile Val Lys Pro Gln Ile Leu Thr His Val Ile Glu
        675                 680                 685

Gly Phe Val Ile Gln Glu Gly Leu Glu Pro Phe Pro Val Ser Arg Ser
    690                 695                 700

Ser Leu Leu Ile Glu Gln Pro Val Lys Lys Arg Pro Leu Leu Asp Asn
705                 710                 715                 720

Gln Val Ile Asn Ser Val Cys Val Gln Pro Glu Leu Gln Asn Asn Thr
                725                 730                 735

Lys His Ala Asp Asn Ser Ser Asp Thr Glu Met Glu Asp Met Ile Ala
            740                 745                 750

Glu Glu Thr Leu Glu Glu Met Asp Ser Glu Leu Leu Lys Cys Glu Phe
        755                 760                 765

Cys Gly Lys Met Gly Tyr Ala Asn Glu Phe Leu Arg Ser Lys Arg Phe
    770                 775                 780

Cys Thr Met Ser Cys Ala Lys Arg Tyr Asn Val Ser Cys Ser Lys Lys
785                 790                 795                 800

Phe Ala Leu Ser Arg Trp Asn Arg Lys Pro Asp Asn Gln Ser Leu Gly
                805                 810                 815

His Arg Gly Arg Arg Pro Ser Gly Pro Asp Gly Ala Ala Arg Glu His
            820                 825                 830

Ile Leu Arg Gln Leu Pro Ile Thr Tyr Pro Ser Ala Glu Glu Asp Leu
        835                 840                 845

Ala Ser His Glu Asp Ser Val Pro Ser Ala Met Thr Thr Arg Leu Arg
    850                 855                 860

Arg Gln Ser Glu Arg Glu Arg Glu Leu Arg Asp Val Arg Ile
865                 870                 875                 880

Arg Lys Met Pro Glu Asn Ser Asp Leu Leu Pro Val Ala Gln Thr Glu
                885                 890                 895

Pro Ser Ile Trp Thr Val Asp Asp Val Trp Ala Phe Ile His Ser Leu
            900                 905                 910
```

```
Pro Gly Cys Gln Asp Ile Ala Asp Glu Phe Arg Ala Gln Glu Ile Asp
        915                 920                 925
Gly Gln Ala Leu Leu Leu Lys Glu Asp His Leu Met Ser Ala Met
    930                 935                 940
Asn Ile Lys Leu Gly Pro Ala Leu Lys Ile Cys Ala Arg Ile Asn Ser
945                 950                 955                 960
Leu Lys Glu Ser

<210> SEQ ID NO 3
<211> LENGTH: 3370
<212> TYPE: DNA
<213> ORGANISM: Mus musculus

<400> SEQUENCE: 3
```

| | |
|---|---|
| tggaggagag aagatggcgg aagcggagtg agtgatggag gagagaagat ggcggaagcg | 60 |
| gagtgagtga cttgctggtt taaggaccac agcacagcta tggatagtga gccgagctct | 120 |
| ggaacatccg tgtcaacaac agccagcagt accaccacca ccaccatcac cacatcctcc | 180 |
| tcccgaatgc agcagccaca gatctctgtc tacagcgggt cagaccgaca tgctgttcag | 240 |
| gtaattcagc aggccttgca tcggcccccc agctcggcag ctcagtacct gcagcagatg | 300 |
| tacgcggctc agcagcagca cctgatgctg cacacggctg ctctgcagca gcagcaccta | 360 |
| agcagctcgc agctccagag ccttgcggct gtccaggcaa gtttgtccag tggaagacca | 420 |
| tctacatccc ccacaggcag tgttacacaa cagtcaagta tgtcccagac atctatcctg | 480 |
| tccgcttctc ctgcacctgc tcagctgatg aaccgctccc agacgtccag ttctaccagc | 540 |
| ggcagtatta cccagcagac tatgctactc gggagtacct ctcccaccct aactgccagc | 600 |
| caagcccaga tgtatctccg agctcagatg ctgattttca cacctgctac cactgtggct | 660 |
| gctgtacagt ctgacatccc tgttgtctcg tcgtcaccgt caccttcctg tcagtctgca | 720 |
| gctgctcagt tcagaatttt aaccttacgc agccagaagc tgggtgtctt atctagctca | 780 |
| cagaatggct caccaaaaag cgctggtcaa acccagtcct tgacaatttg ccataataaa | 840 |
| acaacagtga ccagttctaa aatcagccaa cgagaccctt ctccagagag caagaaggga | 900 |
| ggaagcccag gtctggaatc tcggagcacg gccgtcactc ggacatcaag catccaccag | 960 |
| ttaatagcac cagcttcata ttctccaatt cagcctcatt ctctaatcaa acatcagcag | 1020 |
| attcctcttc attcaccacc tcctaaagtt tccatcatc agctgctatt acaacagcaa | 1080 |
| caacagcaaa ttcagccaat cacccttcag agtccaagtc aagatccacc cccatcccag | 1140 |
| cactgtatcc cactcccaaa ccatggcctt tctccggctc ccagtaatgc ccagccgcag | 1200 |
| cattgctccc cagttcagag ccatcctccg cctttaactg tgtctcccaa ccaggcacag | 1260 |
| tccgcacagc agtctgtagt ggtgtctcct ccccccctc attcccaag tcagtctcct | 1320 |
| actataatta tccatccaca agcacttatc cagccacacc ctcttgtgtc ttcagctctt | 1380 |
| caaacagggc caaatttgca gcaggctgct gctgatcagg tacagtccac cgcacagctg | 1440 |
| aatcttccat cccatcttcc acttccagca tcccctgttg tacacattgg ccctgtccag | 1500 |
| cagtctgcct tggtgtcccc tggtcagcag atggtgtccc caacatcaca ccagcagtat | 1560 |
| tcagccctac agtcctctcc aattcccatc gcgaccactc cacagatgtc ggcatctcct | 1620 |
| ccagctcagc tcccaccact gcccttgcag tctatgcagt ctttacaagt gcagcctgaa | 1680 |
| attctatccc agggccaggt tttggtgcag aatgctttgg tgtcagaaga ggagctacct | 1740 |
| gctgcagaag ctttggtcca gttgccattt cagactcttc ctcctccaca gactgttgcg | 1800 |

```
gtaaatctac aagtacagcc gccagcacct gttgatccac cagtggttta tcaagtagaa    1860
gatgtgtgtg aggaagaaat gccagaggag tccgatgagt gtgcaaggat ggacagaacc    1920
cccccacccc ccaccttgtc tccagcagct gtcactgtgg ggaggggaga ggacttgaca    1980
tccgaacatc ctttgttaga gcaagtggag ttgcctgctg tggcctcagt cagtgcttcc    2040
gtgatcaagt ctccatcaga ccccacccat gcctctgctc ctgcacctcc cctcttaatc    2100
cctgctgcct ccaccaggag cagcagcact tctctggcca gcagcactcc cagcctggaa    2160
aacaagcctc cacaggctat tgtgaaacca cagattttga cccacgttat agaaggcttt    2220
gtgattcagg aggggctgga gccgtttcct gtgagtcgat catcactgct gatagaacaa    2280
cctgtgaaga gaggcctct cttggataat caggtggtaa actctgtgtg tgtccagcca    2340
gagttacaga ataacacaaa gcatgcagat aactcatccg acacagagat agaagacatg    2400
atggctgaag agacattgga agaaatggat agcgagttac tcaagtgtga attctgtgga    2460
aaaatgggat atcctaatga attttacgg tccaaacgat tctgtactat gtcatgtgcc    2520
aaaaggtaca acgttagctg ttctaaaaaa tttgcactta gtcgttggaa tcgtaagcct    2580
gataatcaga gtcttgggca tcggggccgt cgtccaagtg gccctgaagg ggcagcaaga    2640
gaacatatcc ttaggcagct tccaattact tatccatctg cagaagaaga cgtggcctct    2700
catgaagatc ctgtgccttc tgctatgacg acccgtctgc gaaggcagag cgagcgggaa    2760
agagagcgag agcttcggga tgtgaggatt aggaagatgc tgagaatag tgacttgctc    2820
ccagtcgcac agactgagcc ctccatatgg acagtcgacg acgtctgggc cttcatccat    2880
tctttgcccg gctgccagga cgttgcagat gagttcaggg cacaagagat tgatgggcag    2940
gccctgctct tgctaaaaga agaccatctc atgagtgcaa tgaacatgaa gctgggccca    3000
gccctgaaga tttgtgcacg catcaactct ctgaaggact cttaacagga gcgaggcttt    3060
gtgcttctca gcccattcct ctcacaaggt gaaggtaaag cctcgctggg attctctcct    3120
gagaatatca gactgatgga ggaaggccga gtgcactggg accgccacgg ccagtgccga    3180
cgtttctctt cagatgtcct aactcatcat acatttttcat aattagtgaa catcggtgac    3240
attaatttta ccacttacat gctacactga aagacttgtt acagaggccc atatttttca    3300
aagaaacatg ttatactaga taatttttta aaggtaatgt ttatcattaa tataaaaaaa    3360
ccttttaaaa                                                          3370
```

<210> SEQ ID NO 4
<211> LENGTH: 963
<212> TYPE: PRT
<213> ORGANISM: Mus musculus

<400> SEQUENCE: 4

```
Met Asp Ser Glu Pro Ser Ser Gly Thr Ser Val Ser Thr Thr Ala Ser
1               5                   10                  15

Ser Thr Thr Thr Thr Thr Ile Thr Thr Ser Ser Ser Arg Met Gln Gln
            20                  25                  30

Pro Gln Ile Ser Val Tyr Ser Gly Ser Asp Arg His Ala Val Gln Val
        35                  40                  45

Ile Gln Gln Ala Leu His Arg Pro Ser Ser Ala Ala Gln Tyr Leu
    50                  55                  60

Gln Gln Met Tyr Ala Ala Gln Gln His Leu Met Leu His Thr Ala
65                  70                  75                  80

Ala Leu Gln Gln Gln His Leu Ser Ser Ser Gln Leu Gln Ser Leu Ala
                85                  90                  95
```

-continued

```
Ala Val Gln Ala Ser Leu Ser Ser Gly Arg Pro Ser Thr Ser Pro Thr
            100                 105                 110

Gly Ser Val Thr Gln Gln Ser Met Ser Gln Thr Ser Ser Ser Thr
        115                 120                 125

Ser Gly Ser Ile Thr Gln Gln Thr Met Leu Leu Gly Ser Thr Ser Pro
    130                 135                 140

Thr Leu Thr Ala Ser Gln Ala Gln Met Tyr Leu Arg Ala Gln Met Leu
145                 150                 155                 160

Ile Phe Thr Pro Ala Thr Thr Val Ala Ala Val Gln Ser Asp Ile Pro
                165                 170                 175

Val Val Ser Ser Ser Pro Ser Pro Ser Cys Gln Ser Ala Ala Ala Gln
                180                 185                 190

Val Gln Asn Leu Thr Leu Arg Ser Gln Lys Leu Gly Val Leu Ser Ser
            195                 200                 205

Ser Gln Asn Gly Ser Pro Lys Ser Ala Gly Gln Thr Gln Ser Leu Thr
    210                 215                 220

Ile Cys His Asn Lys Thr Thr Val Thr Ser Ser Lys Ile Ser Gln Arg
225                 230                 235                 240

Asp Pro Ser Pro Glu Ser Lys Lys Gly Gly Ser Pro Gly Leu Glu Ser
                245                 250                 255

Arg Ser Thr Ala Val Thr Arg Thr Ser Ser Ile His Gln Leu Ile Ala
                260                 265                 270

Pro Ala Ser Tyr Ser Pro Ile Gln Pro His Ser Leu Ile Lys His Gln
            275                 280                 285

Gln Ile Pro Leu His Ser Pro Pro Lys Val Ser His His Gln Leu
    290                 295                 300

Leu Leu Gln Gln Gln Gln Gln Ile Gln Pro Ile Thr Leu Gln Ser
305                 310                 315                 320

Pro Ser Gln Asp Pro Pro Ser Gln His Cys Ile Pro Leu Pro Asn
                325                 330                 335

His Gly Leu Ser Pro Ala Pro Ser Asn Ala Gln Pro Gln His Cys Ser
            340                 345                 350

Pro Val Gln Ser His Pro Pro Leu Thr Val Ser Pro Asn Gln Ala
    355                 360                 365

Gln Ser Ala Gln Gln Ser Val Val Ser Pro Pro Pro His Ser
    370                 375                 380

Pro Ser Gln Ser Pro Thr Ile Ile Ile His Pro Gln Ala Leu Ile Gln
385                 390                 395                 400

Pro His Pro Leu Val Ser Ser Ala Leu Gln Thr Gly Pro Asn Leu Gln
                405                 410                 415

Gln Ala Ala Ala Asp Gln Val Gln Ser Thr Ala Gln Leu Asn Leu Pro
            420                 425                 430

Ser His Leu Pro Leu Pro Ala Ser Pro Val Val His Ile Gly Pro Val
    435                 440                 445

Gln Gln Ser Ala Leu Val Ser Pro Gly Gln Gln Met Val Ser Pro Thr
    450                 455                 460

Ser His Gln Gln Tyr Ser Ala Leu Gln Ser Ser Pro Ile Pro Ile Ala
465                 470                 475                 480

Thr Pro Pro Gln Met Ser Ala Ser Pro Ala Gln Leu Pro Pro Leu
                485                 490                 495

Pro Leu Gln Ser Met Gln Ser Leu Gln Val Gln Pro Glu Ile Leu Ser
            500                 505                 510
```

```
Gln Gly Gln Val Leu Val Gln Asn Ala Leu Val Ser Glu Glu Leu
        515                 520                 525

Pro Ala Ala Glu Ala Leu Val Gln Leu Pro Phe Gln Thr Leu Pro Pro
530                 535                 540

Pro Gln Thr Val Ala Val Asn Leu Gln Val Gln Pro Pro Ala Pro Val
545                 550                 555                 560

Asp Pro Pro Val Val Tyr Gln Val Glu Asp Val Cys Glu Glu Glu Met
                565                 570                 575

Pro Glu Glu Ser Asp Glu Cys Ala Arg Met Asp Arg Thr Pro Pro Pro
            580                 585                 590

Pro Thr Leu Ser Pro Ala Ala Val Thr Val Gly Arg Gly Glu Asp Leu
        595                 600                 605

Thr Ser Glu His Pro Leu Leu Glu Gln Val Glu Leu Pro Ala Val Ala
    610                 615                 620

Ser Val Ser Ala Ser Val Ile Lys Ser Pro Ser Asp Pro Thr His Ala
625                 630                 635                 640

Ser Ala Pro Ala Pro Pro Leu Leu Ile Pro Ala Ala Ser Thr Arg Ser
                645                 650                 655

Ser Ser Thr Ser Leu Ala Ser Ser Thr Pro Ser Leu Glu Asn Lys Pro
            660                 665                 670

Pro Gln Ala Ile Val Lys Pro Gln Ile Leu Thr His Val Ile Glu Gly
        675                 680                 685

Phe Val Ile Gln Glu Gly Leu Glu Pro Phe Pro Val Ser Arg Ser Ser
    690                 695                 700

Leu Leu Ile Glu Gln Pro Val Lys Lys Arg Pro Leu Leu Asp Asn Gln
705                 710                 715                 720

Val Val Asn Ser Val Cys Val Gln Pro Glu Leu Gln Asn Asn Thr Lys
                725                 730                 735

His Ala Asp Asn Ser Ser Asp Thr Glu Ile Glu Asp Met Met Ala Glu
            740                 745                 750

Glu Thr Leu Glu Glu Met Asp Ser Glu Leu Leu Lys Cys Glu Phe Cys
        755                 760                 765

Gly Lys Met Gly Tyr Pro Asn Glu Phe Leu Arg Ser Lys Arg Phe Cys
    770                 775                 780

Thr Met Ser Cys Ala Lys Arg Tyr Asn Val Ser Cys Ser Lys Lys Phe
785                 790                 795                 800

Ala Leu Ser Arg Trp Asn Arg Lys Pro Asp Asn Gln Ser Leu Gly His
                805                 810                 815

Arg Gly Arg Arg Pro Ser Gly Pro Glu Gly Ala Ala Arg Glu His Ile
            820                 825                 830

Leu Arg Gln Leu Pro Ile Thr Tyr Pro Ser Ala Glu Glu Asp Val Ala
        835                 840                 845

Ser His Glu Asp Pro Val Pro Ser Ala Met Thr Thr Arg Leu Arg Arg
    850                 855                 860

Gln Ser Glu Arg Glu Arg Glu Arg Leu Arg Asp Val Arg Ile Arg
865                 870                 875                 880

Lys Met Pro Glu Asn Ser Asp Leu Leu Pro Val Ala Gln Thr Glu Pro
                885                 890                 895

Ser Ile Trp Thr Val Asp Asp Val Trp Ala Phe Ile His Ser Leu Pro
            900                 905                 910

Gly Cys Gln Asp Val Ala Asp Glu Phe Arg Ala Gln Glu Ile Asp Gly
        915                 920                 925
```

```
                                        -continued
Gln Ala Leu Leu Leu Leu Lys Glu Asp His Leu Met Ser Ala Met Asn
        930                 935                 940

Met Lys Leu Gly Pro Ala Leu Lys Ile Cys Ala Arg Ile Asn Ser Leu
945                 950                 955                 960

Lys Asp Ser
```